(12) United States Patent
Mohr et al.

(10) Patent No.: US 7,731,952 B2
(45) Date of Patent: Jun. 8, 2010

(54) AVIRULENT ONCOLYTIC HERPES SIMPLEX VIRUS STRAINS ENGINEERED TO COUNTER THE INNATE HOST RESPONSE

(75) Inventors: Ian Mohr, New York, NY (US); Matthew Mulvey, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 11/166,438

(22) Filed: Jun. 24, 2005

(65) Prior Publication Data

US 2006/0039894 A1 Feb. 23, 2006

Related U.S. Application Data

(60) Provisional application No. 60/582,714, filed on Jun. 24, 2004.

(51) Int. Cl.
*A61K 48/00* (2006.01)
*A61K 39/00* (2006.01)
*C12N 7/01* (2006.01)
*C12N 15/00* (2006.01)

(52) U.S. Cl. ............... 424/93.2; 424/229.1; 435/235.1; 435/320.1

(58) Field of Classification Search .................. None
See application file for complete search history.

(56) References Cited

U.S. PATENT DOCUMENTS

| | | | |
|---|---|---|---|
| 4,769,331 A | 9/1988 | Roizman et al. |
| 4,859,587 A | 8/1989 | Roizman |
| 5,288,641 A | 2/1994 | Roizman |
| 5,328,688 A | 7/1994 | Roizman |
| 5,585,096 A | 12/1996 | Martuza et al. |
| 5,599,691 A | 2/1997 | Roizman |
| 5,728,379 A | 3/1998 | Martuza et al. |
| 5,824,318 A | 10/1998 | Mohr et al. |
| 5,846,707 A | 12/1998 | Roizman |
| 5,846,948 A | 12/1998 | Bruni et al. |
| 5,876,923 A | 3/1999 | Leopardi et al. |
| 5,922,328 A | 7/1999 | Spector et al. |
| 6,071,692 A | 6/2000 | Roizman |
| 6,120,773 A | 9/2000 | Roizman |
| 6,139,834 A | 10/2000 | Martuza et al. |
| 6,172,047 B1 | 1/2001 | Roizman et al. |
| 6,210,926 B1 | 4/2001 | Leopardi et al. |
| 6,218,103 B1 | 4/2001 | Leopardi et al. |
| 6,340,673 B1 | 1/2002 | Roizman et al. |
| 6,379,674 B1 | 4/2002 | Rabkin et al. |
| 6,383,738 B1 | 5/2002 | Bruni et al. |
| 6,537,541 B1 | 3/2003 | Breakefield et al. |
| 6,555,108 B1 | 4/2003 | Breakefield et al. |
| 6,610,287 B1 | 8/2003 | Breakefield et al. |
| 6,635,416 B2 * | 10/2003 | Palese et al. ............... 435/5 |
| 6,699,468 B1 | 3/2004 | Martuza et al. |
| 6,723,511 B2 | 4/2004 | Leopardi et al. |
| 6,770,274 B1 | 8/2004 | Martuza et al. |
| 6,846,670 B2 | 1/2005 | Schwartz et al. |
| 2002/0015944 A1 | 2/2002 | Roizman et al. |
| 2002/0019362 A1 | 2/2002 | Weichselbaum et al. |
| 2002/0127246 A1 | 9/2002 | Rabkin et al. |
| 2002/0155432 A1 | 10/2002 | Schwartz et al. |
| 2002/0187163 A1 | 12/2002 | Johnson et al. |
| 2002/0192822 A1 | 12/2002 | Leopardi et al. |
| 2003/0207829 A9 | 11/2003 | Weichselbaum et al. |
| 2004/0151697 A1 | 8/2004 | Martuza et al. |
| 2004/0228841 A1 | 11/2004 | Martuza et al. |
| 2005/0048491 A1 | 3/2005 | Weichselbaum et al. |
| 2005/0112142 A1 | 5/2005 | Spaete et al. |
| 2005/0232907 A1 | 10/2005 | Rabkin et al. |

OTHER PUBLICATIONS

Cassady et al., J Virol, 1998, 72: 8620-8626.*
Coukos et al., Cancer Gene Therapy, 2000, 7: 275-283.*
Skelly et al., Gene Therapy, 2001, 8: 1840-1846.*
Huard et al., Neuromuscul. Disord., 1997, 7: 299-313, Abstract.*
Lagunoff et al., J. Virol., 1995, 69: 3615-3623.*
Markert et al., "Conditionally Replicating Herpes Simplex virus Mutant, G207 for the Treatment of Malignant Glioma: Results of a Phase I Trial," *Gene Ther*. 7:867-874 (2000).
Mohr, I., "Genetic Metamorphosis of Herpes Simplex Virus-1 Into a Biological Therapeutic for Human Cancer," *Expert. Opin. Biol. Ther*. 3(1):113-125 (2003).
"ICP47_HHV11/ICP47 Protein/US12 Protein," *UniProtKB/Swiss-Prot Entry P03170* (Jul. 1, 1986).

(Continued)

*Primary Examiner*—Ileana Popa
(74) *Attorney, Agent, or Firm*—Fish & Richardson P.C.

(57) ABSTRACT

The present invention relates to an avirulent, oncolytic herpes simplex virus modified from a wild-type herpes simplex virus so that both $\gamma_1 34.5$ genes of the virus have been deleted and each replaced with an interferon-resistance gene that is expressed as an immediate-early gene. The present invention also relates to a pharmaceutical composition that includes the modified herpes simplex virus of the present invention and a pharmaceutically acceptable vehicle for in situ administration to tumor cells. Also provided in the present invention are methods for killing tumor cells in a subject and for immunizing a subject against an infectious disease, cancer, or an autoimmune disease that involve administering to a subject the modified avirulent, oncolytic herpes simplex virus of the present invention.

13 Claims, 13 Drawing Sheets

OTHER PUBLICATIONS

Advani et al., "Replication-Competent, Nonneuroinvasive Genetically Engineered Herpes Virus is Highly Effective in the Treatment of Therapy-Resistant Experimental Human Tumors," *Cancer Res.* 59:2055-2058 (1999).
Ahn et al., "Molecular Mechanism and Species Specificity of TAP Inhibition by Herpes Simplex Virus Protein ICP47," *EMBO J.* 15:3247-3255 (1996).
Andreansky et al., "The Application of Genetically Engineered Herpes Simplex Viruses to the Treatment of Experimental Brain Tumors," *Proc. Natl. Acad. Sci. USA* 93:11313-11318 (1996).
Basler et. al., "The Ebola Virus VP35 Protein Functions as a Type I IFN Antagonist," *Proc. Natl. Acad. Sci. USA* 97(22):12289-12294 (2000).
Beattie et al., "Reversal of the Interferon-Sensitive Phenotype of a Vaccinia Virus Lacking E3L by Expression of the Reovirus S4 Gene," *J. Virol.* 69(1):499-505 (1995).
Bergmann et al., "Influenza Virus NS1 Protein Counteracts PKR-Mediated Inhibition of Replication," *J. Virol.* 74(13):6203-6206 (2000).
Bolovan et al., "ICP34.5 Mutants of Herpes Simplex Virus Type 1 Strain 17syn+ Are Attenuated for Neurovirulence in Mice and for Replication in Confluent Primary Mouse Embryo Cell Cultures," *J. Virol.* 68:48-55 (1994).
Boutell et al., "Herpes Simplex Virus Type 1 Immediate-Early Protein ICP0 and Its Isolated Ring Finger Domain Act As Ubiquitin E3 Ligases In vitro," *J. Virol.* 76(2):841-850 (2002).
Bradley et al., "Ionizing Radiation Improves Survival in Mice Bearing Intracranial High-Grade Gliomas Injected With Genetically Modified Herpes Simplex Virus," *Clin. Cancer Res.* 5:1517-1522 (1999).
Cassady et al., "Second-Site Mutation Outside of the $U_s$10-12 Domain of Delta $\gamma_1$34.5 Herpes Simplex Virus 1 Recombinant Blocks the Shutoff of Protein Synthesis Induced by Activated Protein Kinase R and Partially Restores Neurovirulence," *J. Virol.* 76:942-990 (2002).
Cassady & Gross, "The Herpes Simplex Virus Type 1 $U_s$11 Protein Interacts With Protein Kinase R In Infected Cells and Requires a 30-Amino-Acid Sequence Adjacent to a Kinase Substrate Domain," *J. Virol.* 76(5):2029-2035 (2002).
Chahlavi et al., "Replication-Competent Herpes Simplex Virus Vector G207 and Cisplatin Combination Therapy for Head and Neck Squamous Cell Carcinoma," *Neoplasia* 1:162-169 (1999).
Chambers et al., "Comparison of Genetically Engineered Herpes Simplex Viruses for the Treatment of Brain Tumors in a *scid* Mouse Model of Human Malignant Glioma," *Proc. Natl. Acad. Sci. USA* 92:1411-1415 (1995).
Chatterjee et al., "Effect of Cloned Human Interferons on Protein Synthesis and Morphogenesis of Herpes Simplex Virus," *J. Virol.* 56(2):419-425 (1985).
Chee et al., "Promyelocytic Leukemia Protein Mediates Interferon-Based Anti-Herpes Simplex Virus 1 Effects," *J. Virol.* 77(12):7101-7105 (2003).
Cheng et al., "Dephosphorylation of eIF2α Mediated By The $\gamma_1$34.5 Protein of Herpes Simplex Virus Type 1 is Required for Viral Response to Interferon but is not Sufficient for Efficient Viral Replication," *J. Virol.* 77(18):10154-10161 (2003).
Child et al., "Complementation of Vaccinia Virus Lacking the Double-Stranded RNA-Binding Protein Gene E3L by Human Cytomegalovirus," *J. Virol.* 76(10):4912-4918 (2002).
Chou et al., "Association of a $M_r$ 90,000 Phosphoprotein With Protein Kinase PKR in Cells Exhibiting Enhanced Phosphorylation of Translation Initiation Factor eIF-2α and Premature Shutoff of Protein Synthesis After Infection With $\gamma_1$34.5⁻ Mutants of Herpes Simplex Virus 1," *Proc. Natl. Acad. Sci. USA* 92:10516-10520 (1995).
Chou et al., "Mapping of Herpes Simplex Virus-1 Neurovirulence to $\gamma_1$34.5, a Gene Nonessential for Growth in Culture," *Science* 250:1262-1266 (1990).
Chou & Roizman, "The $\gamma_1$34.5 Gene of Herpes Simplex Virus 1 Precludes Neuroblastoma Cells From Triggering Total Shutoff of Protein Synthesis Characteristic of Programmed Cell Death in Neuronal Cells," *Proc. Natl. Acad. Sci. USA* 89:3266-3270 (1992).

Chung et al., "B-*myb* Promoter Retargeting of Herpes Simplex Virus $\gamma$34.5 Gene-Mediated Virulence Toward Tumor and Cycling Cells," *J. Virol.* 73:7556-7564 (1999).
Coen et al., "Thymidine Kinase-Negative Herpes Simplex Virus Mutants Establish Latency in Mouse Trigeminal Ganglia But Do Not Reactivate," *Proc. Natl. Acad. Sci. USA* 86:4736-4740 (1989).
Davies et al., "The E3L and K3L Vaccinia Virus Gene Products Stimulate Translation Through Inhibition of the Double-Stranded RNA-Dependent Protein Kinase by Different Mechanisms," *J. Virol.* 67(3):1688-1692 (1993).
Delman et al., "Effects of Preexisting Immunity on the Response to Herpes Simplex-Based Oncolytic Viral Therapy," *Hum. Gene Ther.* 11:2465-2472 (2000).
Eidson et al., "Expression of Herpes Simplex Virus ICP0 Inhibits the Induction of Interferon-Stimulated Genes by Viral Infection," *J. Virol.* 76:2180-2191 (2002).
Field & Darby, "Pathogenicity in Mice of Strains of Herpes Simplex Virus Which are Resistant to Acyclovir In Vitro and In Vivo," *Antimicrob. Agents Chemother.* 17(2):209-216 (1980).
Genbank Accession No. X14112 (Apr. 18, 2005).
Goldsmith et al., "Infected Cell Protein (ICP)47 Enhances Herpes Simplex Virus Neurovirulence by Blocking the CD8+ T Cell Response," *J. Exp. Med.* 187:341-348 (1998).
Hakki & Geballe, "Double-Stranded RNA Binding by Human Cytomegalovirus pTRS1," *J. Virol.* 79(12):7311-7318 (2005).
Hatada et al., "Mutant Influenza Viruses with a Defective NS1 Protein Cannot Block the Activation of PKR in Infected Cells," *J. Virol.* 73(3):2425-2433 (1999).
He et al. "The $\gamma_1$34.5 Protein of Herpes Simplex Virus 1 Complexes With Protein Phosphatase 1α to Dephosphorylate the α Subunit of the Eukaryotic Translation Initiation Factor 2 and Preclude the Shutoff of Protein Synthesis by Double-Stranded RNA-Activated Protein Kinase," *Proc. Natl. Acad. Sci. USA* 94:843-848 (1997).
He et al., "Regulation of mRNA Translation and Cellular Signaling by Hepatitis C Virus Nonstructural Protein NS5A," *J. Virol.* 75(11):5090-5098 (2001).
Herrlinger et al., "Pre-Existing Herpes Simplex Virus 1 (HSV-1) Immunity Decreases, But Does Not Abolish, Gene Transfer to Experimental Brain Tumors by a HSV-1 Vector," *Gene Ther.* 5:809-819 (1998).
Honess & Roizman, "Regulation of Herpesvirus Macromolecular Synthesis, 1. Cascade Regulation of the Synthesis of Three Groups of Viral Proteins," *J. Virol.* 14(1):8-19 (1974).
Hunter et al., "Attenuated, Replication-Competent Herpes Simplex Virus Type 1 Mutant G207: Safety Evaluation of Intracerebral Injection in Nonhuman Primates," *J. Virol.* 73:6319-6326 (1999).
Ikeda et al., "Complement Depletion Facilitates the Infection of Multiple Brain Tumors by an Intravascular, Replication-Conditional Herpes Simplex Virus Mutant," *J. Virol.* 74:4765-4775 (2000).
Ikeda et al., "Oncolytic Virus Therapy of Multiple Tumors in the Brain Requires Suppression of Innate and Elicited Antiviral Responses," *Nat. Med.* 5:881-887 (1999).
Imani & Jacobs, "Inhibitory Activity for the Interferon-Induced Protein Kinase is Associated with the Reovirus Serotype 1 σ3 Protein," *Proc. Natl. Acad. Sci. USA* 85:7887-7891 (1988).
Jorgensen et al., "Ionizing Radiation Docs Not Alter the Antitumor Activity of Herpes Simplex Virus Vector G207 in Subcutaneous Tumor Models of Human and Murine Prostate Cancer," *Neoplasia* 3:451-456 (2001).
Kesari et al., "A Neuroattenuated ICP34.5-Deficient Herpes Simplex Virus Type 1 Replicates in Ependymal Cells of the Murine Central Nervous System," *J. Gen. Virol.* 79:525-536 (1998).
Khoo et al., "Characterization of RNA Determinants Recognized by the Arginine- and Proline-Rich Region of Us11, a Herpes Simplex Virus Type 1-Encoded Double-Stranded RNA Binding Protein That Prevents PKR Activation," *J. Virol.* 76:11971-11981 (2002).
Leib et al., "Interferons Regulate the Phenotypes of Wild-Type and Mutant Herpes Simplex Viruses in Vivo," *J. Exp. Med.* 189:663-672 (1999).
Leib et al., "Specific Phenotypic Restoration of an Attenuated Virus by Knockout of a Host Resistance Gene," *Proc. Natl. Acad. Sci. USA* 97:6097-6101 (2000).

Liu et al., "ICP34.5 Deleted Herpes Simplex Virus With Enhanced Oncolytic, Immune Stimulating, and Anti-Tumour Properties," *Gene Ther.* 10:292-303 (2003).

Lium et al., "Repression of the α0 Gene by ICP4 During a Productive Herpes Simplex Virus Infection," *J. Virol.* 70(6):3488-3496 (1996).

Mackem & Roizman, "Structural Features of the Herpes Simplex Virus α Gene 4, 0, and 27 Promoter-Regulatory Sequences Which Confer α Regulation on Chimeric Thymidine Kinase Genes," *J. Virol.* 44(3):939-949 (1982).

Markovitz et al., "The Range and Distribution of Murine Central Nervous System Cells Infected With the $\gamma_1 34.5^-$ Mutant of Herpes Simplex Virus 1," *J. Virol.* 71:5560-5569 (1997).

Martuza, R.L., "Conditionally Replicating Herpes Vectors for Cancer Therapy," *J. Clin. Invest.* 105(7):841-846 (2000).

Martuza et al., "Experimental Therapy of Human Glioma by Means of a Genetically Engineered Virus Mutant," *Science* 252:854-856 (1991).

Mineta et al., "Attenuated Multi-Mutated Herpes Simplex Virus-1 for the Treatment of Malignant Gliomas," *Nat. Med.* 1:938-943 (1995).

Mohr et al., "A Herpes Simplex Virus Type 1 γ34.5 Second-Site Suppressor Mutant That Exhibits Enhanced Growth in Cultured Glioblastoma Cells is Severely Attenuated in Animals," *J. Virol.* 75:5189-5196 (2001).

Mohr & Gluzman, "A Herpesvirus Genetic Element Which Affects Translation in the Absence of the Viral GADD34 Function," *EMBO J.* 15:4759-4766 (1996).

Mohr, I., "Neutralizing Innate Host Defenses to Control Viral Translation in HSV-1 Infected Cells," *Int. Reviews of Immunol.* 23:199-220 (2004).

Mohr, I., "Regulation of Translation Initiation Factor Activity by Multiple Viral Functions in HSV-1 Infected Cells," Department of Microbiology, New York University School of Medicine, Seminar (May 13, 2005) (Abstract).

Mossman & Smiley, "Herpes Simplex Virus ICP0 and ICP34.5 Counteract Distinct Interferon-Induced Barriers to Virus Replication," *J. Virol.* 76(4):1995-1998 (2002).

Mossman et al., "Herpes Simplex Virus Triggers and Then Disarms a Host Antiviral Response," *J. Virol.* 75(2):750-758 (2001).

Mulvey et al., "A Herpesvirus Ribosome-Associated, RNA-Binding Protein Confers a Growth Advantage Upon Mutants Deficient in a GADD34-Related Function," *J. Virol.* 73:3375-3385 (1999).

Mulvey et al., "Full Resistance of Herpes Simplex Virus Type 1-Infected Primary Human Cells to Alpha Interferon Requires Both the Us11 and $\gamma_1 34.5$ Gene Products," *J. Virol.* 78(18):10193-10196 (2004).

Mulvey et al., "Regulation of eIF2α Phosphorylation by Different Functions That Act During Discrete Phases in the Herpes Simplex Virus Type 1 Life Cycle," *J. Virol.* 77(20):10917-10928 (2003).

Nakamura et al., "Multimodality Therapy With a Replication—Conditional Herpes Simplex Virus 1 Mutant That Expresses Yeast Cytosine Deaminase for Intratumoral Conversion of 5-Fluorocytosine to 5-Fluorouracil," *Cancer Res.* 61:5447-5452 (2001).

Nakamura et al., "Regulation of Herpes Simplex Virus $\gamma_1 34.5$ Expression and Oncolysis of Diffuse Liver Metastases by Myb34.5," *J Clin Invest* 109:871-882 (2002).

Nicholl et al., "Activation of Cellular Interferon-Responsive Genes After Infection of Human Cells With Herpes Simplex Virus Type 1," *J. Gen. Virol.* 81:2215-2218 (2000).

Novoa et al., "Feedback Inhibition of the Unfolded Protein Response by *GADD34*-Mediated Dephosphorylation of eIF2α," *J. Cell Biol.* 153:1011-1021 (2001).

Parker et al., "Engineered Herpes Simplex Virus Expressing IL-12 in the Treatment of Experimental Murine Brain Tumors," *Proc. Natl. Acad. Sci. USA* 97:2208-2213 (2000).

Peters et al., "Inhibition of PACT-Mediated Activation of PKR by the Herpes Simplex Virus Type 1 Us11 Protein," *J. Virol.* 76(21):11054-11064 (2002).

Poppers et al., "Identification of a Lytic-Cycle Epstein-Barr Virus Gene Product That Can Regulate PKR Activation," *J. Virol.* 77(1):228-236 (2003).

Poppers et al., "Inhibition of PKR Activation by the Proline-Rich RNA Binding Domain of the Herpes Simplex Virus Type 1 Us11 Protein," *J. Virol.* 74:11215-11221 (2000).

Preston, C.M., "Control of Herpes Simplex Virus Type 1 mRNA Synthesis in Cells Infected with Wild-Type Virus or the Temperature-Sensitive Mutant *tsK*," *J. Virol.* 29(1):275-284 (1979).

Randall et al., "The Product of ORF O Located Within the Domain of Herpes Simplex Virus 1 Genome Transcribed During Latent Infection Binds to and Inhibits In vitro Binding of Infected Cell Protein 4 to Its Cognate DNA Site," *Proc. Natl. Acad. Sci. USA* 94:10379-10384 (1997).

Roberts et al., "Direct Correlation Between a Negative Autoregulatory Response Element at the Cap Site of the Herpes Simplex Virus Type1 IE175 (α4) Promoter and a Specific Binding Site for the IE175 (ICP4) Protein," *J. Virol.* 62(11):4307-4320 (1988).

Roller & Roizman, "The Herpes Simplex Virus 1 RNA Binding Protein $U_s11$ Is a Virion Component and Associates With Ribosomal 60S Subunits," *J. Virol.* 66(6):3624-3632 (1992).

Sourvinos & Everett, "Visualization of Parental HSV-1 Genomes and Replication Compartments in Association with ND10 in Live Infected Cells," *EMBO J.* 21(18):4989-4997 (2002).

Sundaresan et al., "Attenuated, Replication-Competent Herpes Simplex Virus Type 1 Mutant G207: Safety Evaluation in Mice," *J. Virol.* 74:3832-3841 (2000).

Taneja et al., "Enhanced Antitumor Efficacy of a Herpes Simplex Virus Mutant Isolated by Genetic Selection in Cancer Cells," *Proc. Natl. Acad. Sci. USA* 98(15):8804-8808 (2001).

Toda et al., "Herpes Simplex Virus as an In Situ Cancer Vaccine for the Induction of Specific Anti-Tumor Immunity," *Hum. Gene Ther.* 10:385-393 (1999).

Todo et al., "In Situ Expression of Soluble B7-1 in the Context of Oncolytic Herpes Simplex Virus Induces Potent Antitumor Immunity," *Cancer Res.* 61:153-161 (2001).

Todo et al., "Oncolytic Herpes Simplex Virus Vector With Enhanced MHC Class I Presentation and Tumor Cell Killing," *Proc. Natl. Acad. Sci. USA* 98:6396-6401 (2001).

Todo et al., "Systemic Antitumor Immunity in Experimental Brain Tumor Therapy Using a Multimutated, Replication-Competent Herpes Simplex Virus," *Hum. Gene Ther.* 10:2741-2755 (1999).

Van Sant et al., "The Infected Cell Protein 0 of Herpes Simplex Virus 1 Dynamically Interacts With Proteasomes, Binds and Activates the cdc34 E2 Ubiquitin-Conjugating Enzyme, and Possesses In vitro E3 Ubiquitin Ligase Activity," *Proc. Natl. Acad. Sci. USA* 98(15):8815-20 (2001).

Wang et al., "E3 Gene Manipulations Affect Oncolytic Adenovirus Activity in Immunocompetent Tumor Models," *Nat. Biotech.* 21:1328-1335 (2003).

Wong et al., "Effective Intravenous Therapy of Murine Pulmonary Metastases With an Oncolytic Herpes Virus Expressing Interleukin 12," *Clinical Cancer Research* 10:251-259 (2004).

York et al., "A Cytosolic Herpes Simplex Virus Protein Inhibits Antigen Presentation to $CD8^+$ T Lymphocytes," *Cell* 77:525-535 (1994).

Yu et al., "Visualization of Tumors and Metastases in Live Animals With Bacteria and Vaccinia Virus Encoding Light-Emitting Proteins," *Nat. Biotech.* 22:313-320 (2004).

Zhou et al., "Engineered Herpes Simplex Virus 1 is Dependent on IL13Rα2 Receptor for Cell Entry and Independent of Glycoprotein D Receptor Interaction," *Proc. Natl. Acad. Sci. USA* 99:15124-15129 (2002).

* cited by examiner

AVIRULENT ONCOLYTIC HERPES SIMPLEX VIRUS STRAINS ENGINEERED TO COUNTER THE INNATE HOST RESPONSE

This application claims benefit of U.S. Provisional Patent Application Ser. No. 60/582,714, filed Jun. 24, 2004, which is hereby incorporated by reference in its entirety.

The subject matter of this application was made with support from the United States Government under the National Institutes of Health Grant No. RO1GM056927. The U.S. Government may retain certain rights.

FIELD OF THE INVENTION

The present invention relates to an oncolytic avirulent modified herpes simplex virus having a high level of replication in neoplastic cells, and uses thereof for immunization against and treatment of disease conditions.

BACKGROUND OF THE INVENTION

One hundred years ago, the first anecdotal observations correlating viral infection with tumor regression were reported, which lead to several investigations, over the course of the last century, evaluating the potential of various natural human and animal viruses to treat cancer. (Sinkovics et al., "New Developments in the Virus Therapy of Cancer: A Historical Review," *Intervirology* 36:193-214 (1993)). These observations suggest that malignant lesions could regress in response to viral infection. To be effective in treatments of malignancies, such isolates should only grow productively and exhibit virulence in neoplastic cells, and should not be capable of propagating a productive infection through surrounding normal, terminally differentiated tissue. As virulence is governed by specific viral genes, one approach would be to genetically alter the virulence of viruses to obtain viruses which selectively destroy neoplastic cells. However, it was the achievements of the last two decades, most notably technical innovation in the area of molecular biology coupled with a heightened understanding of viral replication and pathogenesis at the genetic level, which ushered in the possibility of creating viruses in the laboratory which were selectively pathogenic for neoplastic cells. The advent of genetic engineering techniques has made it possible to selectively ablate viral virulence genes in the hope of creating a safe, avirulent virus that can selectively replicate in and destroy tumor cells. Such a virus would be able to propagate an infection throughout a tumor mass and directly kill the cancer cells, but be unable to inflict substantial damage to normal terminal differentiated cells. Although safe viruses have been created by such methodology, the attenuation process often has an overall deleterious effect on viral replication. This replication defect prevents the virus from completely destroying the tumor mass, and the surviving cancer cells can simply repopulate.

HSV-1 is a double-stranded DNA virus which is replicated and transcribed in the nucleus of the cell. HSV-1 consists of at least three groups of genes, α, β, and γ, whose expression is coordinately regulated and sequentially ordered in a cascade fashion. (Honess et al., "Regulation of Herpesvirus Macromolecular Synthesis, I. Cascade Regulation of the Synthesis of Three Groups of Viral Proteins," *J Vir* 14:8-19 (1974)). Five immediate early (IE or α) genes are the first genes expressed during productive infection. While one of these genes encodes the immunomodulatory protein ICP47, the remaining four α genes encode infected cell proteins (ICPs) 0, 4, 22, and 27, the major regulatory proteins of the virus. These immediate early proteins then activate the expression of viral genes of the early (E or β) and late (L or γ) classes. Once the viral lifecycle advances beyond the IE stage, the ICP4 protein also autoregulates IE gene expression by reducing transcription from IE promoters (Preston, "Control of Herpes Simplex Virus Type 1 mRNA Synthesis in Cells Infected with Wild-Type Virus or the Temperature-Sensitive Mutant tsK," *J Vir* 29: 275-284 (1979); Roberts et al., "Direct Correlation Between a Negative Autoregulatory Response Element at the Cap Site of the Herpes Simplex Virus Type1 IE175(α4) Promoter and a Specific Binding Site for the IE175 (α4) Protein," *J Vir* 62: 4307-4320 (1988); Lium et al., "Repression of the alpha0 gene by ICP4 During a Productive Herpes Simplex Virus Infection," *J Vir* 70: 3488-3496 (1996)). Proteins of the E class are responsible for viral DNA replication. The late (L) genes are induced after DNA replication and encode the structural components and enzymes required for assembly of virus particles.

Following infection of oral epithelial cells in its human host, HSV-1 invades axons and travels to the nuclei of sensory neurons that innervate this epithelia. Here, the virus establishes a latent infection, characterized by a restricted pattern of viral gene expression. (Roizman et al., "Herpes Simplex Viruses and Their Replication," in: Knipe et al., eds. *Fields Virology* Vol. 2, 4th Ed., Philadelphia, Pa.: Lippincott, Williams & Wilkins, pp. 2399-2460 (2001)). Latency results in the permanent colonization of the host by the virus, and the severely limited expression of viral genes functions to shield the virus from host defenses.

In response to a variety of stimuli, these latent infections "reactivate," resulting in episodes of productive viral growth characterized by expression of over 80 viral open reading frames (ORFs) distributed among two unique, single copy segments or within multiple repetitive loci of the large HSV-1 DNA genome. Activation of the productive or lytic gene expression program results in the production of viral particles and the eventual death of the infected cell. Distinct mRNA populations accumulate at discrete times in the productive replication cycle, resulting in the differential expression of viral genes in what has been termed a cascade pattern. (Roizman et al., "Herpes Simplex Viruses and Their Replication," in: Knipe et al., eds. *Fields Virology* Vol. 2, 4th Ed., Philadelphia, Pa.: Lippincott, Williams & Wilkins, pp. 2399-2460 (2001)). The process is initiated by VP16, a transcription factor carried within the viral particle that recruits cellular transcription factors along with the RNA polymerase II holoenzyme to the promoters of the five viral IE genes. While one of these IE gene products dampens the host immune response by inhibiting the presentation of peptide antigens in conjunction with MHC class I molecules (Us12), the remaining four IE proteins are important for the subsequent expression of the next class of viral genes, the early or β genes. Viral early polypeptides primarily encode functions required for nucleotide metabolism and viral DNA synthesis, the initiation of which signals entry into the final late or γ phase of the viral life cycle. Two classes of late genes have been identified based upon their transcription in the presence of viral DNA synthesis inhibitors. While transcription of a subset of γ genes, the $\gamma_2$ class, requires viral DNA synthesis, expression of $\gamma_1$ genes is not completely dependent upon viral DNA replication and is only modestly reduced in the presence of inhibitors. Included among the late gene products are polypeptides critical for assembling infectious virus, virion components that function following entry but before IE gene expression, and proteins that regulate the host response to infection. Reactivation of a latent infection in a sensory neuron results in antereograde transport of viral progeny back to the portal of entry followed by the ensuing infection of epithelial cells, mobilization of the cellular immune response, and the formation of a fever blister or cold sore. Rarely, HSV-1 can enter and replicate within the CNS, causing encephalitis.

Martuza and colleagues were the first to demonstrate the therapeutic promise of an engineered oncolytic HSV-1 strain, the thymidine kinase (tk) negative HSV-1 mutant, dlsptk. (Martuza et al., "Experimental Therapy of Human Glioma by Means of a Genetically Engineered Virus Mutant," *Science* 252:854-856 (1991)). tk mutants replicate effectively in actively dividing cells such as those found in tumors, but are relatively impaired for replication in non-dividing cells, such as neurons, and, therefore, display reduced neurovirulence compared with wild-type strains upon introduction into the CNS of adult mice. (Field et al., "The Pathogenicity of Thymidine Kinase-Deficient Mutants of Herpes Simplex Virus in Mice," *J Hyg* (*Lond*) 81:267-277 (1978); Jamieson et al., "Induction of Both Thymidine and Deoxycytidine Kinase Activity by Herpes Viruses," *J Gen Virol* 24:465-480 (1974); Field et al., "Pathogenicity in Mice of Strains of Herpes Simplex Virus Which are Resistant to Acyclovir In Vitro and In Vivo," *Antimicrob Agents Chemother* 17:209-216 (1980); Tenser et al, "Trigeminal Ganglion Infection by Thymidine Kinase-Negative Mutants of Herpes Simplex Virus," *Science* 205:915-917 (1979); Coen et al., "Thymidine Kinase-Negative Herpes Simplex Virus Mutants Establish Latency in Mouse Trigeminal Ganglia But Do Not Reactivate," *Proc Natl Acad Sci USA* 86:4736-4740 (1989)). The tumor selected for oncolytic therapy was malignant glioma. The outcome for patients with this devastating brain tumor is grim, remaining essentially unchanged over the past 50 years despite advances in surgery, radiation, and chemotherapy. Direct injection of dlsptk into established tumors inhibited the growth of human glioma implants in athymic mice and prolonged survival of mice with intracranial gliomas as well. However, fatal encephalitis was still observed in 70-100% of the treated mice despite the fact that the tk mutant was significantly less neurovirulent than wild-type HSV-1. (Martuza et al., "Experimental Therapy of Human Glioma by Means of a Genetically Engineered Virus Mutant," *Science* 252:854-856 (1991)). Thus, while it proved possible to use HSV-1 as an oncolytic virus to destroy cancer cells, the understanding of virulence was not sufficiently advanced to render the virus safe.

The breakthrough in creating attenuated HSV-1 strains resulted from characterizing viruses containing engineered mutations in the $\gamma_1 34.5$ genes. Embedded within a repetitive genome component, the $\gamma_1 34.5$ gene is expressed with $\gamma_1$ late kinetics and is not required for growth in cultured monkey kidney cells (Vero cells). Strikingly, its impact on viral neurovirulence is greater than any single HSV-1 gene identified to date. (Chou et al., "Mapping of Herpes Simplex Virus-1 Neurovirulence to Gamma (1) 34.5, a Gene Nonessential for Growth in Culture," *Science* 250:1262-1266 (1990); Maclean et al., "Herpes Simplex Virus Type 1 Deletion Variants 1714 and 1716 Pinpoint Neurovirulence-Related Sequences in Glasgow Strain 17+ Between Immediate Early Gene 1 and the 'a' Sequence," *J Gen Virol* 72:631-639 (1991); Bolovan et al., "ICP34.5 Mutants of Herpes Simplex Virus Type 1 Strain 17syn+ Are Attenuated for Neurovirulence in Mice and for Replication in Confluent Primary Mouse Embryo Cell Cultures," *J Virol* 68:48-55 (1994)). While the $LD_{50}$ of many wild-type (WT) HSV-1 strains is less than 300 pfu following intracranial delivery, it is not possible to accurately measure the $LD_{50}$ for $\gamma 34.5$ mutant viruses. Indeed, upwards of $10^6$-$10^7$ pfu of $\gamma 34.5$ mutant viruses have been safely injected intracranially into mouse, non-human primate, and human brains (Chou et al., "Mapping of Herpes Simplex Virus-1 Neurovirulence to Gamma (1) 34.5, a Gene Nonessential for Growth in Culture," *Science* 250:1262-1266 (1990); Maclean et al., "Herpes Simplex Virus Type 1 Deletion Variants 1714 and 1716 Pinpoint Neurovirulence-Related Sequences in Glasgow Strain 17+ Between Immediate Early Gene 1 and the 'a' Sequence," *J Gen Virol* 72:631-639 (1991); Bolovan et al., "ICP34.5 Mutants of Herpes Simplex Virus Type 1 Strain 17syn+ Are Attenuated for Neurovirulence in Mice and for Replication in Confluent Primary Mouse Embryo Cell Cultures," *J Virol* 68:48-55 (1994); Mineta et al., "Attenuated Multi-Mutated Herpes Simplex Virus-1 for the Treatment of Malignant Gliomas," *Nat Med* 1:938-943 (1995); Hunter et al., "Attenuated, Replication-Competent Herpes Simplex Virus Type 1 Mutant G207: Safety Evaluation of Intracerebral Injection in Nonhuman Primates," *J Virol* 73:6319-6326 (1999); Markert et al., "Conditionally Replicating Herpes Simplex Virus Mutant, G207 for the Treatment of Malignant Glioma: Results of a Phase 1 Trial," *Gene Ther* 7:867-874 (2000); Rampling et al., "Toxicity Evaluation of Replication-Competent Herpes Simplex Virus (ICP 34.5 Null Mutant 1716) in Patients With Recurrent Malignant Glioma," *Gene Ther* 7:859-866 (2000); Sundaresan et al., "Attenuated, Replication-Competent Herpes Simplex Virus Type 1 Mutant G207: Safety Evaluation in Mice," *J Virol* 74:3832-3841 (2000)). In studies designed to examine the efficacy with which $\gamma 34.5$ mutants were able to destroy human or murine gliomas implanted into mice, not only had the attenuation problem been solved, but the treated mice survived longer than their untreated counterparts and no longer developed viral encephalitis. Long-term surviving animals (usually in the vicinity of 60-80 days) were produced with efficiencies ranging from 10-50% of the treated animals depending on the tumor model and treatment regimen. (Markert et al., "Reduction and Elimination of Encephalitis in an Experimental Glioma Therapy Model with Attenuated Herpes Simplex Mutants That Retain Susceptibility To Acyclovir," *Neurosurgery* 32:597-603 (1993); Chambers et al., "Comparison of Genetically Engineered Herpes Simplex Viruses for the Treatment of Brain Tumors in a SCID Mouse Model of Human Malignant Glioma," *Proc Natl Acad Sci USA* 92:1411-1415 (1995); Kesari et al., "Therapy of Experimental Human Brain Tumors Using a Neuroattenuated Herpes Simplex Virus Mutant," *Lab Invest* 73:636-648 (1995); Andreansky et al., "The Application of Genetically Engineered Herpes Simplex Viruses to the Treatment of Experimental Brain Tumors," *Proc Natl Acad Sci USA* 93:11313-11318 (1996); Andreansky et al., "Evaluation of Genetically Engineered Herpes Simplex Viruses as Oncolytic Agents for Human Malignant Brain Tumors," *Cancer Res* 57:1502-1509 (1997); Randazzo et al., "Treatment of Experimental Intracranial Murine Melanoma With a Neuroattenuated Herpes Simplex Virus 1 Mutant," *Virology* 211:94-101 (1995) of Human Malignant Glioma," *Proc Natl Acad Sci USA* 92(5):1411-1415(1995)). $\gamma 34.5$ mutants were also tk+ and, therefore, retained their sensitivity to acyclovir, which could be used, if necessary, to control viral encephalitis. To further restrict viral replication to actively dividing cells, additional mutations in the $U_L 39$ ribonucleotide reductase gene or the $U_L 2$ uracil DNA glycosidase gene were introduced into the $\gamma_1 34.5$ mutant background (Mineta et al., "Attenuated Multi-Mutated Herpes Simplex Virus-1 for the Treatment of Malignant Gliomas," *Nat Med* 1:938-943 (1995); Kramm et al., "Therapeutic Efficiency and Safety of a Second-Generation Replication-Conditional HSV 1 Vector for Brain Tumor Gene Therapy," *Hum Gene Ther* 8:2057-2068 (1997); Pyles et al., "A Novel Multiply-Mutated HSV-1 Strain for the Treatment of Human Brain Tumors," *Hum Gene Ther* 8:533-544 (1997)). Although each of these non-neurovirulent, multi-mutated viruses could reduce subcutaneous tumor growth and extend the survival of mice with intracranial tumors, more than 80% of the treated subjects still succumbed, emphasizing a different problem limiting the efficacy and outcome of treatment. While encephalitis was no longer observed in animals treated with any of these $\gamma_1 34.5$ mutant derivatives, the $\gamma_1 34.5$ deletion, either alone or in conjunction with additional mutations, impaired the replicative ability of these viruses in many human tumor cells, allowing the growth of residual glioma cells that ultimately killed the animals. Thus, the successful attenuation of HSV-1 left in its wake another problem for investigators to grapple with: engineered mutants that were sufficiently safe had lost a substantial amount of their replicative efficacy, impairing their oncolytic ability.

The reduced oncolytic ability of $\gamma_1 34.5$ mutant derivatives results from their inability to counter an innate host defense designed to inhibit protein synthesis in virus-infected cells. After the initial reports established that the $\gamma_1 34.5$ gene was a major determinant of HSV-1 neurovirulence non-essential for growth in cultured monkey kidney cells, further investigation revealed that $\gamma_1 34.5$ mutants actually behaved like classical viral host range mutants, exhibiting restricted growth in some lines of cultured cells but not others. Thus, while a standard line of monkey kidney cells were permissive or supported the replication $\gamma_1 34.5$ mutants, many human tumor cells were non-permissive, or did not support the growth of $\gamma_1 34.5$ mutant derivatives. Upon infection of a non-permissive human tumor cell with a $\gamma_1 34.5$ mutant strain, all of the events in the viral lifecycle proceeded normally up to and including viral DNA replication and the accumulation of $\gamma_2$ late mRNA transcripts. These viral late mRNAs encoding key structural proteins required to complete the viral lifecycle and assemble the next generation of viral progeny, however, were never translated due to a block at the level of protein synthesis, effectively interrupting the viral lifecycle prior to the assembly and release of viral particles (Chou et al., "The Gamma (1) 34.5 Gene of Herpes Simplex Virus 1 Precludes Neuroblastoma Cells From Triggering Total Shutoff of Protein Synthesis Characteristic of Programmed Cell Death in Neuronal Cells," *Proc Natl Acad Sci USA* 89:3266-3270 (1992)). Subsequent biochemical analysis demonstrated that the $\gamma_1 34.5$ gene product was required to prevent accrual of phosphorylated eIF2, a critical translation initiation factor required to bring the initiator tRNA to the ribosome. Phosphorylation of eIF2 on its alpha subunit inactivates this translation factor and inhibits protein synthesis (Chou et al., "Association of a M(r) 90,000 Phosphoprotein With Protein Kinase PKR in Cells Exhibiting Enhanced Phosphorylation of Translation Initiation Factor eIF-2 Alpha and Premature Shutoff of Protein Synthesis After Infection With Gamma (1) 34.5-Mutants of Herpes Simplex Virus 1," *Proc Natl Acad Sci USA* 92:10516-10520 (1995)). Thus, the inability of $\gamma_1 34.5$ mutants to sustain protein synthesis in tumor cells limits their potential efficacy as replicating oncolytic viruses.

As obligate intracellular parasites, viruses are completely dependent upon the translational machinery resident in their host cells. It is not surprising, therefore, that a major innate host defense component centers on impeding viral mRNA translation. Indeed, the double-stranded RNA-dependent protein kinase PKR, an eIF2α kinase, is induced by the antiviral cytokines interferon α/β. It has been proposed that abundant dsRNA, a replicative intermediate formed in the replication of RNA viruses and a by-product of overlapping transcription units on opposite DNA strands of DNA viruses, is a signature of viral infection. PKR binds dsRNA and, in the presence of this activating ligand, forms a dimer, whereupon each subunit phosphorylates the other. It is this activated, phosphorylated form of PKR that then goes on to phosphorylate other substrates, including eIF2α, the regulatory subunit of eIF2 (Kaufman R J, "Double-Stranded RNA-Activated Protein Kinase PKR," In: Sonenberg eds. *Translational Control*. Cold Spring Harbor, N.Y.: Cold Spring Harbor Laboratory Press, 503-528 (2000)). Should cells initially infected succeed in inhibiting translation, the viral invader would effectively be stopped in its tracks, denied access to the cellular translational apparatus it needs to complete its lifecycle. This arm of the innate host response, then, is designed to sacrifice the initially infected cells for the benefit of the larger population. Any effective oncolytic virus must be able to thwart host defenses if it is to propagate an infection throughout a tumor causing regression and, ultimately, the destruction of the tumor. Failure to mount an effective response against both innate and acquired host defenses is likely to prevent viral replication and subsequent spread throughout the tumor tissue. The present invention describes how to engineer an attenuated $\gamma_1 34.5$ mutant virus that is capable of countering both the acquired immune response and the innate host responses mediated by interferon.

At least two herpes simplex virus gene products have been implicated in the virus's ability to resist the pleiotropic effects of interferon (IFN). One of these is the product of the ICP0 gene, a multifunctional polypeptide produced very early in the viral life cycle that transactivates viral gene expression (Everett, R. D., "ICP0, A Regulator of Herpes Simplex Virus During Lytic and Latent Infection," *Bioessays* 22:761-770 (2000)). ICP0 deficient mutants are hypersensitive to IFN, as viral mRNAs do not accumulate in IFN treated Vero cells, whereas cellular mRNAs encoding IFN induced gene products increase in abundance (Eidson et al., "Expression of Herpes Simplex Virus ICP0 Inhibits the Induction of Interferon-Stimulated Genes by Viral Infection," *J Virol* 76:2180-2191 (2002), Mossman et al., "Herpes Simplex Virus Triggers and Then Disarms a Host Antiviral Response," *J Virol* 75:750-758 (2001), Mossman et al., "Herpes Simplex Virus ICP0 and ICP34.5 Counteract Distinct Interferon-Induced Barriers To Virus Replication," *J Virol* 76:1995-1998 (2002), Nicholl et al., "Activation of Cellular Interferon-Responsive Genes After Infection of Human Cells With Herpes Simplex Type 1," *J Gen Virol* 81:2215-2218 (2000)). This particular IFN antiviral effect requires the cellular promyelocytic leukemia (PML) gene product, and it has been proposed that the disassembly of PML bodies observed in HSV-1 infected cells, which requires the ubiquitin E3 ligase activity of ICP0 (Boutell et al., "Herpes Simplex Virus Type 1 Immediate-Early Protein ICP0 And Its Isolated RING Finger Domain Act As Ubiquitin E3 Ligases in vitro," *J Virol* 76:841-850 (2002), Van Sant et al., "The Infected Cell Protein 0 of Herpes Simplex Virus 1 Dynamically Interacts With Proteasomes, Binds And Activates The cdc34 E2 Ubiquitin-Conjugating Enzyme, And Possesses In Vitro E3 Ubiquitin Ligase Activity," *Proc Natl Acad Sci USA* 98:8815-20 (2001)), enables the virus to prevent the induction of IFN responsive genes (Chee et al., "Promyelocytic Leukemia Protein Mediates Interferon-Based Anti-Herpes Simplex Virus 1 Effects," *J Virol* 77:7101-7105 (2003)). While the ICP0 polypeptide prevents the transcriptional induction of cellular IFN responsive genes, the $\gamma_1 34.5$ gene, when altered, results in an IFN hypersensitive virus, encodes a product that operates by preventing host defenses from inactivating the critical translation initiation factor eIF2 (Cerveny et al., "Amino Acid Substitutions In The Effector Domain of The γ₁34.5 Protein of Herpes Simplex Virus I Have Differential Effects On Viral Response To Interferon-α," *Virology* 307:290-300 (2003), Cheng et al., "Val¹⁹³ and Phe¹⁹⁵ of The γ₁34.5 Protein of Herpes Simplex Virus 1 Are Required For Viral Resistance To Interferon α/β," *Virology* 290:115-120 (2001), Mossman et al., "Herpes Simplex Virus ICP0 and ICP34.5 Counteract Distinct Interferon-Induced Barriers To Virus Replication," *J Virol* 76:1995-1998 (2002)).

Upon binding the catalytic subunit of protein phosphatase1α (PP1α), the γ₁34.5-PP1α holoenzyme prevents the accumulation of phosphorylated, inactive eIF2α in infected cells, preserving viral translation rates (He et al., "The Gamma(1)34.5 Protein of Herpes Simplex Virus 1 Complexes With Protein Phosphatase 1 Alpha To Dephosphorylate The Alpha Subunit of Eukaryotic Initiation Factor 2 And Preclude The Shutoff of Protein Synthesis By Double-Stranded RNA-Activated Protein Kinase," *Proc Natl Acad Sci USA* 94:843-848 (1997)). However, in many established human cell lines infected with a γ₁34.5 mutant virus, the onset of viral DNA synthesis and the accumulation of γ₂ late viral mRNA transcripts are accompanied by the complete cessation of cellular and viral protein synthesis (Chou et al., "The γ34.5 Gene of Herpes Simplex Virus 1 Precludes Neuroblastoma Cells From Triggering Total Shutoff of Protein Synthesis Characteristic of Programmed Cell Death In Neuronal Cells," *Proc Natl Acad Sci USA* 89:3266-3270 (1992)). Thus, γ₁34.5 mutants are not only deficient in functions intrinsic to the γ₁34.5 gene product, but, by failing to translate the viral γ₂ mRNAs, they are also deficient in all the activities encoded by this entire class of genes as well. Importantly, when dealing with phenotypes ascribed to a deficiency in the γ₁34.5 gene, it is fair to question whether the failure to translate these late γ₂ viral mRNAs contributes to the observed phenotype. One of these late γ₂ mRNAs encodes the Us11 polypeptide, a dsRNA binding (Khoo et al., "Characterization of RNA Determinants Recognized by The Arginine- and Proline-Rich Region of Us11, A Herpes Simplex Virus Type 1-Encoded Double-Stranded RNA Binding Protein That Prevents PKR Activation," *J Virol* 76:11971-11981 (2002)), ribosome-associated protein (Roller et al., "The Herpes Simplex Virus 1 RNA Binding Protein Us11 Is A Virion Component And Associates With 60S Ribosomal Subunits," *J Virol* 66:3624-3632 (1992)) that physically associates with PKR (Cassady et al., "The Herpes Simplex Virus Type 1 Us11 Protein Interacts With Protein Kinase R In Infected Cells and Requires a 30 Amino Acid Sequence Adjacent to a Kinase Substrate Domain," *J Virol* 76:2029-2035 (2002); Poppers et al., "Identification of a Lytic-Cycle Epstein-Barr Virus Gene Product That Can Regulate PKR Activation," *J Virol* 77:228-236 (2003)) and can prevent PKR activation in response to dsRNA and PACT, a cellular protein that can activate PKR in an RNA independent manner (Peters et al., "Inhibition of PACT-Mediated Activation of PKR By The Herpes Simplex Virus Type 1 Us11 Protein," *J Virol* 76:11054-11064 (2002)). Furthermore, Us11 can preclude the premature cessation of protein synthesis observed in cells infected with a γ₁34.5 mutant when it is expressed at immediate-early, as opposed to late times, post-infection (Mohr et al., "A Herpesvirus Genetic Element Which Affects Translation In The Absence of The Viral GADD34 Function," *EMBO J* 15:4759-4766 (1996); Mulvey et al., "A Herpesvirus Ribosome Associated, RNA-Binding Protein Confers A Growth Advantage Upon Mutants Deficient in a GADD34-Related Function," *J Virol* 73:3375-3385 (1999)). Recently, it was demonstrated that the premature cessation of translation observed in cells infected with a γ₁34.5 mutant actually results from the combined loss of γ₁34.5 function along with the failure to translate the Us11 mRNA, establishing that HSV-1 utilizes different mechanisms to regulate eIF2α phosphorylation at discrete phases of the viral life cycle (Mulvey et al., "Regulation of eIF2α Phosphorylation By Different Functions That Act During Discrete Phases In The HSV-1 Lifecycle," *J Virol* 77:10917-10928 (2003)).

Numerous replication-competent, attenuated herpes simplex virus-1 (HSV-1) derivatives that contain engineered mutations into the viral γ34.5 virulence gene have been used as oncolytic agents. (U.S. Pat. Nos. 5,328,688 and 6,071,692 to Roizman; U.S. Pat. No. 5,824,318 to Mohr et al.; Mulvey et al., "Regulation of eIF2α Phosphorylation By Different Functions That Act During Discrete Phases In The HSV-1 Lifecycle," *J Virol* 77:10917-10928 (2003); (Taneja et al., "Enhanced Antitumor Efficacy of a Herpes Simplex Virus Mutant Isolated by Genetic Selection in Cancer Cells," *Proc Natl Acad Sci USA* 98:8804-08 (2001); Markert et al., "Genetically Engineered HSV in the Treatment of Glioma: A Review," *Rev Med Virol* 10(1):17-30 (2000); Martuza et al., "Conditionally Replicating Herpes Vectors for Cancer Therapy," *J Clin Invest* 105(7):841-846 (2000); Andreansky et al., "The Application of Genetically Engineered Herpes Simplex Viruses to the Treatment of Experimental Brain Tumors," *Proc Natl Acad Sci USA* 93(21): 11313-8 (1996); Kesari et al., "Therapy of Experimental Human Brain Tumors Using a Neuroattenuated Herpes Simplex Virus Mutant," *Lab Invest* 73(5):636-648 (1995); Mineta et al., "Attenuated Multi-Mutated Herpes Simplex Virus-1 for the Treatment of Malignant Gliomas," *Nature Medicine* 1(9):938-43 (1995); Chambers et al., "Comparison of Genetically Engineered Herpes Simplex Viruses for the Treatment of Brain Tumors in SCID Mouse Model of Human Malignant Glioma," *Proc Natl Acad Sci USA* 92(5):1411-1415(1995)). However, a major limitation in the use of attenuated, replication-competent viruses to directly destroy tumors continues to be the reduced growth of these weakened strains in many cell types, including cancer cells. Despite an initial wave of oncolysis, host defenses trigger an inability of the viral vector to replicate successfully for long enough to eradicate the entire population of neoplastic cells, and the surviving cancer cells reestablish their strangle-hold on the patient.

What is needed now is a thorough understanding of the contribution made by the Us11 gene towards the overall IFN-resistant phenotype of HSV-1, and the application of that information to the making of improved, more efficacious viral anti-tumor agents.

The present invention is directed to overcoming these and other deficiencies in the art.

SUMMARY OF THE INVENTION

The present invention relates to an avirulent, oncolytic herpes simplex virus that is modified from a wild-type herpes simplex virus so that both γ₁34.5 genes of the virus have been deleted and each replaced with an interferon-resistance gene that is expressed as an immediate-early gene.

The present invention also relates to a pharmaceutical composition that includes an avirulent oncolytic herpes simplex virus modified from a wild-type herpes simplex virus so that both γ₁34.5 genes of the virus have been deleted and each replaced with an interferon-resistance gene that is expressed as an immediate-early gene. The pharmaceutical composition also includes a pharmaceutically acceptable vehicle for in situ administration to tumor cells.

The present invention also relates to a method for killing tumor cells in a subject. This method involves administering to a subject a pharmaceutical composition including an avirulent, oncolytic herpes simplex virus modified from a wild-type herpes simplex virus so that both $\gamma_1 34.5$ genes of the virus have been deleted and each replaced with an interferon-resistance gene that is expressed as an immediate-early gene. The pharmaceutical composition also includes a pharmaceutically acceptable vehicle for in situ administration to tumor cells. The administration of the pharmaceutical composition is carried out under conditions effective to kill tumors cells in the subject.

Another aspect of the present invention is a method of immunizing a subject against an infectious disease, cancer, or an autoimmune disease. This method involves administering to a subject an avirulent, oncolytic herpes simplex virus modified from a wild-type herpes simplex virus so that the $\gamma_1 34.5$ genes of the virus have been deleted and each replaced with an interferon-resistance gene that is expressed as an immediate-early gene, and a pharmaceutically acceptable vehicle. The administering to the subject is carried out under conditions effective to immunize the subject against an infectious disease, cancer, or an autoimmune disease.

The modified herpes simplex virus of the present invention is engineered for expression of the Us11 gene product during the immediate-early phase of the viral life-cycle, preferably without inactivating the Us12 gene, thus preserving the ability of the virus to inhibit the host-acquired immune response. Furthermore, it also retains the ability to express Us11 as a late gene, allowing for continual, sustained delivery of an anti-interferon function throughout the entire productive viral replication cycle. This is significant, as the expression of the IE Us11 genes will be negatively regulated by ICP4, whereas the endogenous Us11 gene under the control of a late promoter is not repressed by ICP4. Because the modified virus of the present invention can counteract the innate host response mediated by interferon, it is far more successful at replicating in cancer cells than the currently utilized $\gamma_1 34.5$ deletion viruses, and, therefore, provides a superior agent for tumor killing and for immunization against infectious and proliferative disease conditions.

BRIEF DESCRIPTION OF THE DRAWINGS

FIG. 2A shows that HSV-1 possesses a linear dsDNA genome composed of two sections: the Unique Long ($U_L$) and Unique Short ($U_s$), each represented by solid black lines flanked by open boxes on the top of each page. The boxes represent the inverted terminal repeats that flank the $U_L$ and $U_s$ ($TR_L$ and $TR_s$). The letters above the representation of the genome identify the BamHI restriction enzyme digestion fragments which contain the γ34.5 and Us11 loci. The thick black lines between and below selected restriction sites indicate the probes used in southern blotting. The horizontal arrows indicate various transcription units and the stars represent their respective promoters. The boxes below the horizontal lines denote open reading frames (ORF), the names of which are printed within the boxes. The γ34.5 locus is diploid because it is contained within the $TR_L$ repeats, while the Us11 locus is haploid because it is located in the $U_s$ region. Both γ34.5 loci can be distinguished by size after BamHI digestion and southern blotting, because the first γ34.5 locus is wholly contained within the BamHI S fragment, whereas the second, larger locus is comprised of a fusion between the terminal BamHI S and P fragments. This fusion fragment is termed Bam SP. The γ34.5 ORF is situated between the NcoI and SacI sites and is transcribed by a promoter (indicated by star) located between the DraI and NcoI sites. FIG. 2B is a diagram of the Δ34.5 modified virus, in which both copies of the $\gamma_1 34.5$ gene are replaced by sequences encoding β-glucuronidase.

FIG. 3A is an exposure of the fixed, dried gel. FIG. 3B, bottom panel, shows an immunoblot of the samples probed with a polyclonal antibody raised against the $\gamma_1 34.5$ protein. The arrowhead to the right of the blot denotes the position of the full-length $\gamma_1 34.5$ polypeptide encoded by the HSV-1 Patton strain. The migration of molecular weight standards (in kilodaltons) appears to the left of each panel.

FIG. 4A is an SDS-PAGE gel of protein isolated from FS4 cells treated with PAA in the presence and absence of IFNα, infected with the indicated viruses (as described in legend for FIG. 3), metabolically labeled with $^{35}S$ amino acids for 1 hour at 14 hours post-infection, and processed as described for FIG. 3A. In the lower panel, samples were analyzed by immunoblotting using anti-PKR antisera. FIG. 4B is an SDS-PAGE gel of proteins isolated from FS4 cells, either untreated or treated with PAA, infected with the indicated viruses and processed as described in the examples. The lower panel shows an immunoblot of the samples that was probed with an anti-gC (late protein) polyclonal antibody.

FIG. 7A is a detailed map showing the restriction endonuclease fragments used to make the modified virus in exploded view (dotted lines). The fragments are denoted by different line markings in FIG. 7A to aid in interpreting the southern blots in FIG. 8 showing the restriction mapping of the modified virus Δ34.5::f1α27P-Us11. FIG. 7B is a simple line diagram of the Δ34.5::f1α27P-Us11 genome showing the location of the three copies of the US11 gene in the modified virus.

DETAILED DESCRIPTION OF THE INVENTION

Figure 1:
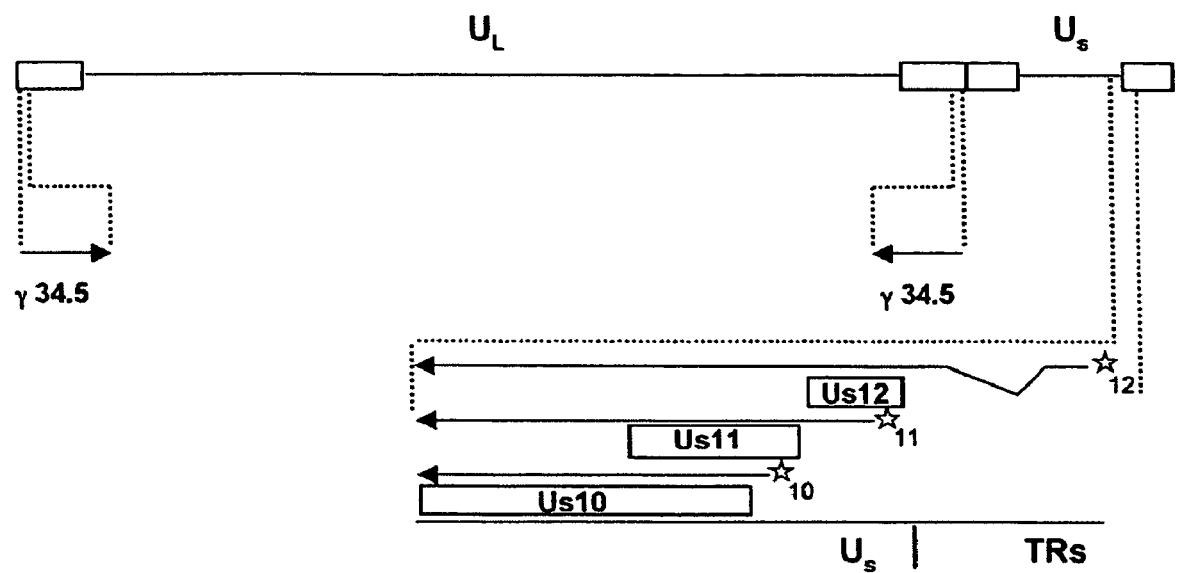
FIG. 1 is a line diagram of the wild-type HSV-1 genome. Boxed regions designate inverted terminal repeat (TR) regions that flank the unique short (Us) and unique long ($U_L$) components, represented by solid lines. Dotted lines indicate an expanded view of a region of the genome. The Us-TRs junction region containing the Us10, Us11, and Us12 open reading frames (ORFs), designated by open rectangles, appears expanded. Stars represent the respective cis-acting promoter elements. The arrow above each box extending from the promoter element denotes the mRNA transcript that encodes each gene product. All of these mRNAs are polyadenylated at a common polyadenylation signal (not depicted) downstream from the Us10 ORF. The Us12 mRNA is spliced, as indicated by the dip in the arrow joining two non-contiguous regions to form the mRNA.

The present invention relates to an avirulent, oncolytic herpes simplex virus that is modified from a wild-type herpes simplex virus so that both $\gamma_1$34.5 genes of the virus have been deleted and each is replaced with an interferon-resistance gene that is expressed as an immediate-early gene. It also retains the ability to express an anti-interferon gene, exemplified by Us11, as a late gene and can counteract the acquired immune response through the action of the Us12 gene product. The modified virus is non-neurovirulent and replicates in and destroys neoplastic cells.

The optimal intracellular environment for virus replication develops through events that begin to take place with attachment of virus to the cell membrane. Binding of the herpes simplex virus to the cell membrane receptor(s) is followed by a cascade of events that are associated with biochemical, physiological, and morphological changes in the cells. Following infection in susceptible cells, lytic replication is regulated by a temporally coordinated sequence of gene transcription. Binding of the virus to a host cell membrane activates the immediate-early (IE or α) genes (ICP0, ICP4, ICP22, ICP27, and ICP47), which are transactivating factors allowing the production of next group of genes to be transcribed, the early (β) genes. Expression of immediate-early gene products is followed by the expression of proteins encoded by the early and then, the late (γ) genes. The entire cascade of gene activation and viral replication in the WT virus takes about 18 hours and invariably results in cell death. The modified HSV mutant of the present invention circumvents the protein synthesis shutoff phenotype of $\gamma_1$34.5 deletion viruses, creating a more robust $\gamma_1$34.5 deletion virus. In WT HSV, the US11 gene product binds to RNA and is expressed with true late ($\gamma_2$) kinetics. However, the modified virus of the present invention has two Us11 genes placed under the control of an IE gene promoter. Us11 expressed an IE gene compensates for deletions in $\gamma_1$34.5, in that eIF-2α is not phosphorylated and protein translation is not inhibited. Thus, the modified HSV of the present invention overcomes PKR-mediated protein synthesis shutoff. As a result, the modified virus of the present invention, having both $\gamma_1$34.5 genes replaced with Us11 having IE gene kinetics, replicates to a higher titer compared to other $\gamma_1$34.5 null virus mutants, and has greater efficacy as an avirulent oncolytic agent.

Exemplary viral interferon resistance genes with which both HSV $\gamma_1$34.5 genes are replaced in the modified oncolytic virus of the present invention include, without limitation, the HSV Us11 gene, which, as described in greater detail herein, is an interferon antagonist. Interferon antagonists encoded by other viruses can also be utilized, as it is likely that many viruses can counteract host interferons (He et al., "Regulation of mRNA Translation and Cellular Signaling by Hepatitis C Nonstructural Protein NS5A," *J Virol* 75: 5090-5098 (2001); Basler et. al., "The Ebola virus VP35 protein functions as a type I IFN antagonist," *Proc Natl Acad Sci USA* 97:12289-12294 (2000); Hakki et al., "Double-Stranded RNA Binding by Human Cytomegalovirus pTRS1," *J Virol* 79: 7311-7318 (2005), which are hereby incorporated by reference in their entirety). As more antagonists are identified in other viruses, they can be incorporated into the present invention as well. Significantly, it is well established that interferon antagonists from one virus can function to provide an anti-interferon function when incorporated into the genome of a heterologous virus (He et al., "Regulation of mRNA Translation and Cellular Signaling by Hepatitis C Nonstructural Protein NS5A," *J Virol* 75: 5090-5098 (2001); Basler et al., "The Ebola virus VP35 Protein Functions as a Type I IFN Antagonist," *Proc Natl Acad Sci USA* 97: 12289-12294 (2000); Beattie et al., "Reversal of the Interferon-Sensitive Phenotype of a Vaccinia Virus Lacking E3L by Expression of the Reovirus S4 Gene," *J Virol* 69: 499-505 (1995); Child et al., "Complementation of Vaccinia Virus Lacking the Double-Stranded RNA-Binding Protein Gene E3L by Human Cytomegalovirus," *J Virol* 76: 4912-4918 (2002), which are hereby incorporated by reference in their entirety). Other suitable interferon resistance genes include, without limitation, the influenza NS1 gene (Bergmann et al., "Influenza Virus NS1 Protein Counteracts PKR-Mediated Inhibition of Replication," *J Virol* 74:6203-6 (2000); Garcia-Sastre et al., "Influenza A Virus Lacking the NS1 Gene Replicates in Interferon-Deficient Systems," *Virology* 252:324-30 (1998); Hatada et al., "Mutant Influenza Viruses with a Defective NS1 Protein Cannot Block the Activation of PKR in Infected Cells," *J Virol* 73:2425-33 (1999), which are hereby incorporated by reference in their entirety), the vaccinia E3L gene (Davies et al., "The E3L and K3L Vaccinia Virus Gene Products Stimulate Translation Through Inhibition of the Double-Stranded RNA-Dependent Protein Kinase by Different Mechanisms," *J Virol* 67:1688-92 (1993); Beattie et al., "Distinct Patterns of IFN Sensitivity Observed in Cells Infected with Vaccinia K3L- and E3L-Mutant Viruses," *Virology* 210:254-63(1995);

Beattie et al., "Host-Range Restriction of Vaccinia Virus E3L-Specific Deletion Mutants," *Virus Genes* (12:89-94 (1996); Beattie et al., "Reversal of the Interferon-Sensitive Phenotype of a Vaccinia Virus Lacking E3L by Expression of the Reovirus S4 Gene," *J Virol* 69:499-505 (1995), which are hereby incorporated by reference in their entirety), the reovirus sigma 3 gene (Imani et al., "Inhibitory Activity for the Interferon-Induced Protein Kinase is Associated with the Reovirus Serotype 1 sigma 3 Protein," *Proc Natl Acad Sci USA* 85:7887-91 (1988), which is hereby incorporated by reference in its entirety), and the adenovirus virus associated RNAs (Ad VA RNAs) (Mori et al., "Anti-Interferon Activity of Adenovirus-2-Encoded VAI and VAII RNAs in Translation in Cultured Human Cells," *Virus Res* 42:53-63 (1996), which is hereby incorporated by reference in its entirety).

The interferon-resistance genes which replace the $\gamma_1 34.5$ virulence genes in the oncolytic modified virus of the present invention are placed under the control of immediate-early promoter. Exemplary promoters for this aspect of the present invention include, without limitation, the herpes simplex virus immediate-early promoters α27, α4, α0, α22, and α47.

In another aspect of the present invention, interferon-resistance genes which replace the $\gamma_1 34.5$ virulence genes in the oncolytic modified herpes simplex virus of the present invention are placed under the control of an early (or β) promoter including without limitation the herpes simplex virus early promoters from the following genes: ICP8 (or $U_L 29$), thymidine kinase (tk or $U_L 23$), ICP6 ($U_L 39$) or any of the DNA replication genes.

In one aspect of the present invention, the oncolytic modified virus of the present invention described above includes an intact (i.e., non-inactivated) herpes simplex virus Us11 gene, which is expressed as a late gene under the control of its naturally-occurring late promoter, or under the control of any other late expressing promoter. Since ICP4 only represses IE promoters, Us11 expressed from a late promoter is not expressed by ICP4.

In another aspect of the present invention, the oncolytic modified virus of the present invention includes an intact (i.e., non-inactivated) herpes simplex virus Us12 gene ensuring that the acquired immune response directed against HSV-1 can be properly controlled. The Us112 gene product (also known as the ICP47 protein or the α47 protein) is an important immunomodulatory protein. The binding of the Us12 gene product to the transporter associated with antigen presentation (TAP) blocks antigenic peptide transport in the lumen of the endoplasmic reticulum and prevents loading of MHC class I molecules (York et al., "A Cytosolic Herpes Simplex Virus Protein Inhibits Antigen Presentation to CD8+ T Lymphocytes," *Cell* 77:525-535 (1994); Hill et al., "Herpes Simplex Virus Turns Off the TAP to Evade Host Immunity," *Nature* 375:411-415 (1995); Ahn et al., "Molecular Mechanism and Species Specificity of TAP Inhibition By Herpes Simplex Virus ICP47," *EMBO J* 15:3247-3255 (1996), which are hereby incorporated by reference in their entirety). The binding of the Us12 protein is species specific for TAPs from large animals, with the affinity for murine TAP about 100-fold less than the affinity for human TAP (Ahn et al., "Molecular Mechanism and Species Specificity of TAP Inhibition By Herpes Simplex Virus ICP47," *EMBO J* 15:3247-3255 (1996), which is hereby incorporated by reference in its entirety). Although the absence of Us12 function in other oncolytic viruses (i.e., SUP1, G47Δ, R47Δ) will result in increased presentation of viral antigens on the surface of infected cell, this might, on the one hand, lead to a more robust immune response against tumor antigens generating a systemic response capable of eradicating not only cells within the primary, treated tumor, but micro-metastases that have disseminated to distant sites as well. Alternatively, and equally likely, the absence of Us12 might result in increased clearance of the oncolytic virus, effectively eliminating the infection and its chances of spreading through the tumor. The reduced efficiency with which Us12 functions in a mouse makes it difficult to test which of these alternatives will prevail in an animal model (Ahn et al., "Molecular Mechanism and Species Specificity of TAP Inhibition By Herpes Simplex Virus ICP47," *EMBO J* 15:3247-3255 (1996), which is hereby incorporated by reference in its entirety).

In another aspect of the present invention, the modified HSV of the present invention includes an ICP6-inactivating mutation or insertion. ICP6 is an infected-cell protein encoded by the UL39 ribonucleotide reductase gene. (Mineta et al., "Attenuated Multi-Mutated Herpes Simplex Virus-1 for the Treatment of Malignant Gliomas," Nat Med 1:938-943 (1995); Kramm et al., "Therapeutic Efficiency and Safety of a Second-Generation Replication-Conditional HSV1 Vector for Brain Tumor Gene Therapy," Hum Gene Ther 8:2057-2068 (1997), which are hereby incorporated by reference in their entirety). ICP6 is the large subunit of ribonucleotide reductase, a key enzyme for nucleotide metabolism and viral synthesis in non-dividing, but not actively dividing cells. Thus, to further restrict viral replication to actively dividing cells, additional mutations in the UL39 ribonucleotide reductase gene or the UL2 uracil DNA glycosidase gene are introduced into the background of the modified HSV of the present invention (Pyles et al., "A Novel Multiply-Mutated HSV-1 Strain for the Treatment of Human Brain Tumors," Hum Gene Ther 8:533-544 (1997), which is hereby incorporated by reference in its entirety). The $\gamma_1 34.5$ deletion virus in which ICP6 is also inactivated results in a mutant having a minimal chance of reverting to wild-type, preferential replication in tumor cells, attenuated neurovirulence, and ganciclovir/acyclovir hypersensitivity Mineta et al., "Attenuated Multi-Mutated Herpes Simplex Virus-1 for the Treatment of Malignant Gliomas," *Nat Med* 1:938-943 (1995), which is hereby incorporated by reference in its entirety).

In one aspect of the present invention the oncolytic modified virus of the present invention includes mutant viruses that are genetically modified wild-type herpes simplex viruses, including, without limitation, HSV-1 and HSV-2. This includes, for example HSV-1 strain F, strain Patton, strain 17, strain KOS, and strain MP. For HSV-2, this includes strain G, and strain HG52. Of all the herpes viruses, herpes simplex virus type 1 and herpes simplex virus type 2 are the most closely related, with nearly 70 percent genomic homology. These two viruses can be distinguished most reliably by DNA composition; however, differences in antigen expression and biologic properties also serve as methods for differentiation. In addition, isolates of HSV-1 and HSV-2 that may be identified clinically are encompassed by the present invention.

The present invention also relates to a pharmaceutical composition that includes a pharmaceutically acceptable vehicle for in situ administration to tumor cells and the avirulent, oncolytic herpes simplex virus of the present invention, modified from a wild-type herpes simplex virus so that the $\gamma_1 34.5$ genes of the virus have been deleted and each replaced with an interferon-resistance gene that is expressed as an immediate-early gene, as described herein above and in greater detail in the Examples, below.

The present invention also relates to a method for killing tumor cells in a subject. This method involves administering to a subject the avirulent, oncolytic modified herpes simplex virus of the present invention and a pharmaceutically acceptable vehicle for in situ administration to tumor cells. The modified virus of this aspect is made as described herein. In situ administration of the modified virus of the present invention is the preferable therapeutic strategy in order to limit cell lysis to the site of the neoplastic cell proliferation. Also suitable in this and other aspects of the present invention are methods of administration that involve specific targeting of the pharmaceutical composition to a desired site, for example, a tumor or other tissue that is the site of excess cellular proliferation. In this aspect, the method would also include providing a target-specific moiety (e.g., antibody or cell marker) suitable for targeted administration of the modified virus of the present invention to the desired tissue.

In this aspect of the present invention, the tumor cells subject to killing by oncolysis include, without limitation, astrocytoma, oligodendroglioma, meningioma, neurofibroma, glioblastoma, ependymoma, Schwannoma, neurofibrosarcoma, and medulloblastoma, melanoma cells, pancreatic cancer cells, prostate carcinoma cells, breast cancer cells, lung cancer cells, colon cancer cells, lymphoma cells, hepatoma cells, mesothelioma, and epidermoid carcinoma cells.

In this and all aspects of the present invention involving administration to a subject, the modified oncolytic virus of the present invention can be administered by injection, infusion, instillation, or inhalation, orally, subcutaneously, intravenously, intramuscularly, intraperitoneally, or by application to mucous membranes, such as that of the nose, throat, and bronchial tubes.

For in situ administration to a tumor or other site of excessive cellular proliferation, the avirulent, oncolytic modified herpes simplex virus of the present invention may be administered in injectable dosages by solution or suspension of the inhibitor in a sterile, physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, such a glycerols, and glycols, such as propylene glycol or polyethylene glycol, are preferred liquid carriers, particularly for injectable solutions. In all cases, the form must be sterile and must be fluid to the extent that easy syringability exists. It must be stable under the conditions of manufacture and storage and must be preserved against the contaminating action of microorganisms, such as bacteria and fungi.

For use as aerosols, the modified oncolytic virus of the present invention provided in solution or suspension may be packaged in a pressurized aerosol container together with suitable propellants, for example, hydrocarbon propellants like propane, butane, or isobutane with conventional adjuvants. Administration may also be carried out with the modified virus of the present invention in a non-pressurized form such as in a nebulizer or atomizer.

In this and all aspects of the present invention the subject is any mammal, including, but not limited to, humans.

Another aspect of the present invention is a method of immunizing a subject against an infectious disease, cancer, or an autoimmune disease. This method involves administering to a subject a pharmaceutical composition having an oncolytic herpes simplex virus modified from a wild-type herpes simplex virus so that the virus's $\gamma_1 34.5$ genes have been deleted and each is replaced with an interferon-resistance gene that is expressed as an immediate-early gene, where the modified virus is avirulent and replicates in and destroys neoplastic or other excessively proliferating cells. The composition also includes a pharmaceutically acceptable vehicle for in situ administration to the subject. Administering the composition to the subject thereby immunizes the subject against an infectious disease, cancer, or an autoimmune disease.

Administration of the pharmaceutical composition in this aspect of the present invention, making of the modified virus, and suitable subjects are as described herein above for other aspects of the present invention.

EXAMPLES

Example 1

Determination of Us11 as an Interferon Resistance Gene

To ascertain the importance of the Us11 gene product in the ability of HSV-1 to replicate in IFNα treated cells, a panel of previously constructed mutant herpes simplex viruses were employed (Mulvey et al., "Regulation of eIF2α Phosphorylation By Different Functions That Act During Discrete Phases In The HSV-1 Lifecycle," *J Virol* 77:10917-10928 (2003), which is hereby incorporated by reference in its entirety). The wild-type HSV-1 genome, shown as a line diagram in FIG. 1, is 152 Kb in length and is composed of a unique long segment ($U_L$), a unique short segment (Us), shown as solid lines, and inverted terminal repeat (TR) regions, shown as open rectangles, that flank the Us and $U_L$ components. Dotted lines indicate an expanded view of a region. The location and orientation of both copies of the $\gamma_1 34.5$ virulence gene are indicated. The $\gamma_1 34.5$ gene is contained within the repetitive components that flank the $U_L$ segment, thus, the WT HSV-1 is diploid for this gene. The Us-TRs junction region containing the Us10, Us11, and Us12 open reading frames (ORFs) is shown in exploded view in the lower portion of FIG. 1. The RNA's that are synthesized from the these genes appear as arrows above the open reading frames. Promoter elements that direct the synthesis of these RNA's appear as stars and each promoter is normally (i.e., in a non-modified, naturally-occurring virus) associated with either the Us10, Us11, or Us12 ORF (denoted by the number 10, 11, or 12 at the lower right of each star).

Figure 2A:
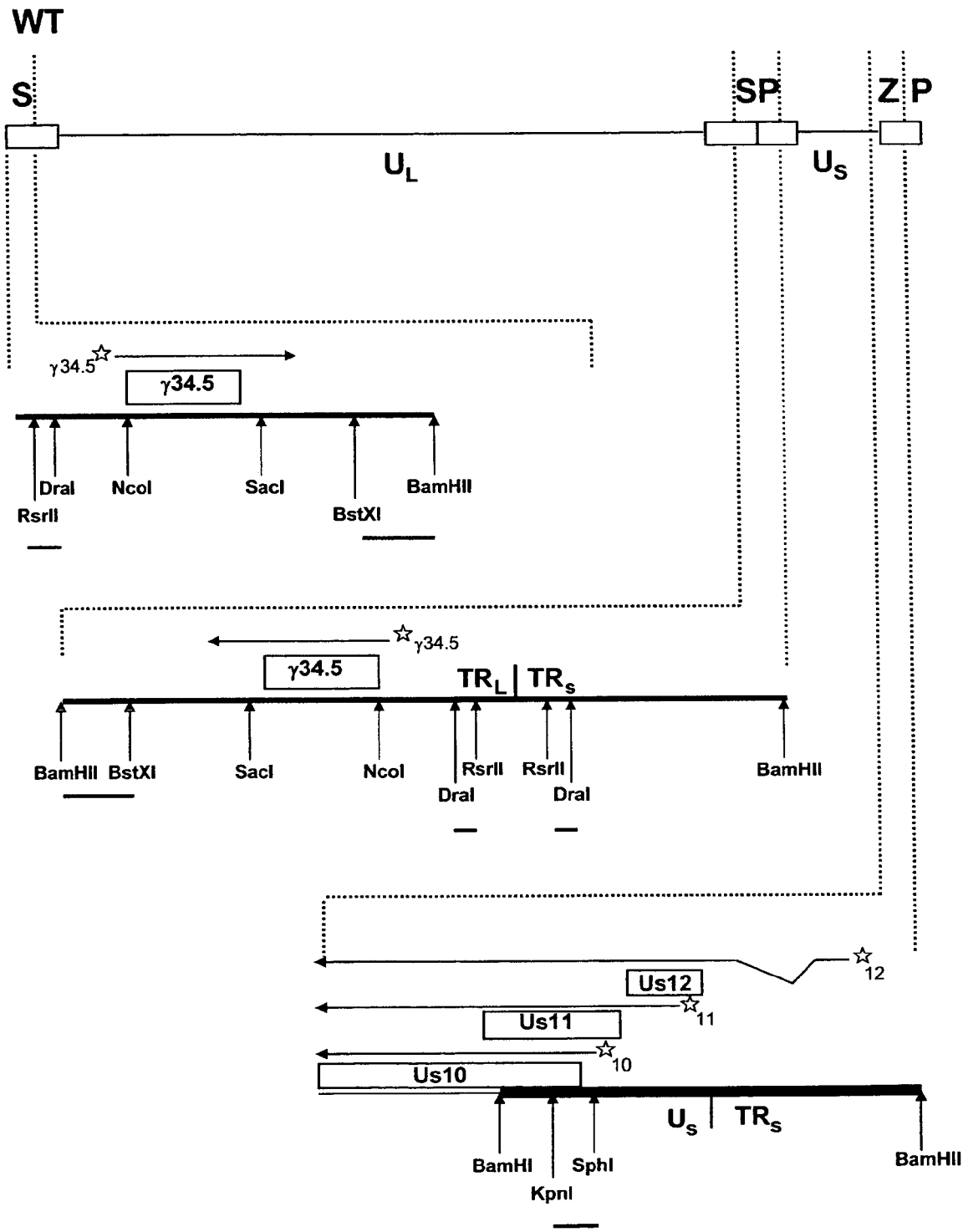
FIGS. 2A and 2B are detailed maps of the genome of wild-type HSV-1 and the Δ34.5 modified (deletion mutant) virus, respectively.
Figure 2B:
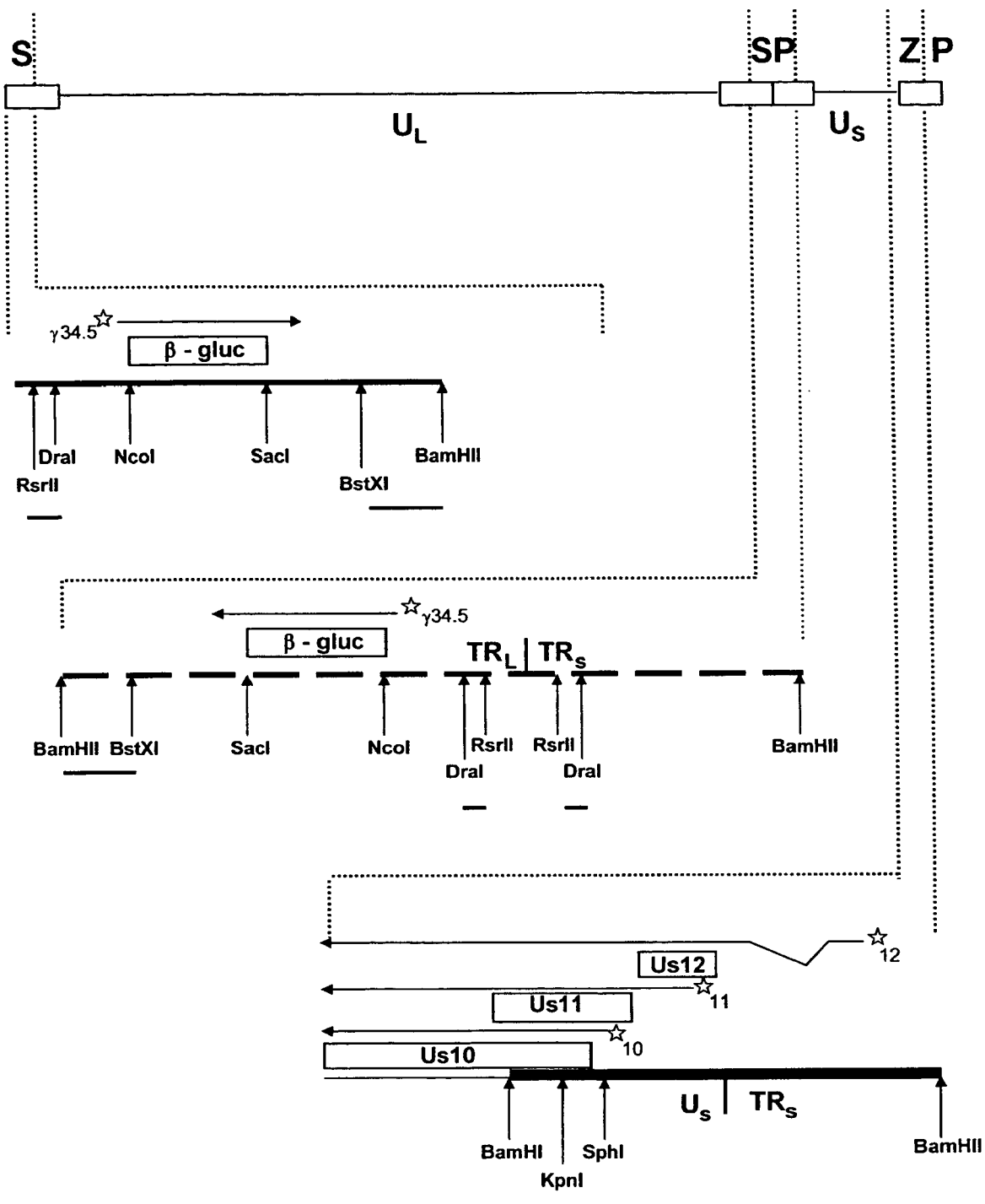

The making of modified HSV vectors can be followed by referring to FIG. 2A, which is a line diagram of the HSV-1 genome in expanded detail, showing restriction sites used in the preparation of modified HSV vectors (Mohr et al., "A Herpesvirus Genetic Element Which Affects Translation In The Absence of The Viral GADD34 Function," *EMBO J* 15:4759-4766 (1996); (Mulvey et al., "Regulation of eIF2α Phosphorylation By Different Functions That Act During Discrete Phases In The HSV-1 Lifecycle," *J Virol* 77:10917-10928 (2003), which are hereby incorporated by reference in their entirety) to produce the Δ34.5 mutant, the Δ34.5 (IE) Us11 mutant, and the pAUs11 mutant by modifications to the HSV-1 virus. Briefly, Δ34.5 is a $\gamma_1 34.5$ null (deletion) mutant, in which both copies of the $\gamma_1 34.5$ gene are replaced by sequences encoding β-glucuronidase. Δ34.5 was generated by placing the β-glucuronidase gene between the NcoI and SacI sites (Mohr et al., "A Herpesvirus Genetic Element Which Affects Translation In The Absence of The Viral GADD34 Function," *EMBO J* 15:4759-4766 (1996); which is hereby incorporated by reference in its entirety), thereby deleting the $\gamma_1 34.5$ ORF and placing β-glucuronidase under transcriptional control of the $\gamma_1 34.5$ promoter. This modified (mutant) herpes simplex virus is shown in detail in FIG. 2B.

The mutant Δ34.5-(IE)Us11 virus was isolated by selecting γ₁34.5 suppressor variants (a spontaneous mutation) capable of replicating in cells that failed to support the growth of the parental γ₁34.5 mutant. In addition to the Δ34.5 deletion mutation, the replication-competent Δ34.5-(IE)Us11 contains a 583-bp deletion that removes most of the Us12 ORF, including the initiator AUG codon, and that spans the adjoining Us-TRs junction. As the Us11 γ₂ promoter is contained within the deleted segment of the Us12 ORF, the deletion also results in the translation of the Us11 protein from an mRNA that initiates from the Us12 IE promoter (Mulvey et al., "Regulation of eIF2α Phosphorylation By Different Functions That Act During Discrete Phases In The HSV-1 Lifecycle," *J Virol* 77:10917-10928 (2003), which is hereby incorporated by reference in its entirety). Thus, Δ34.5-(IE)Us11 mutant expresses Us11 as an immediate-early protein as opposed to a γ₂ late protein. pAUs11 is a Us11 null mutant. The pAUs11-Rep is a mutant in which the Us11 mutation was repaired to generate genotypically WT HSV-1 viruses. The isolation of viruses in which the introduced mutations were repaired to their WT state ensures that any phenotypes observed are due to the introduced mutations rather than secondary, cryptic mutations (Mulvey et al., "Regulation of eIF2α Phosphorylation By Different Functions That Act During Discrete Phases In The HSV-1 Lifecycle," *J Virol* 77:10917-10928 (2003), which is hereby incorporated by reference in its entirety).

Figure 3:
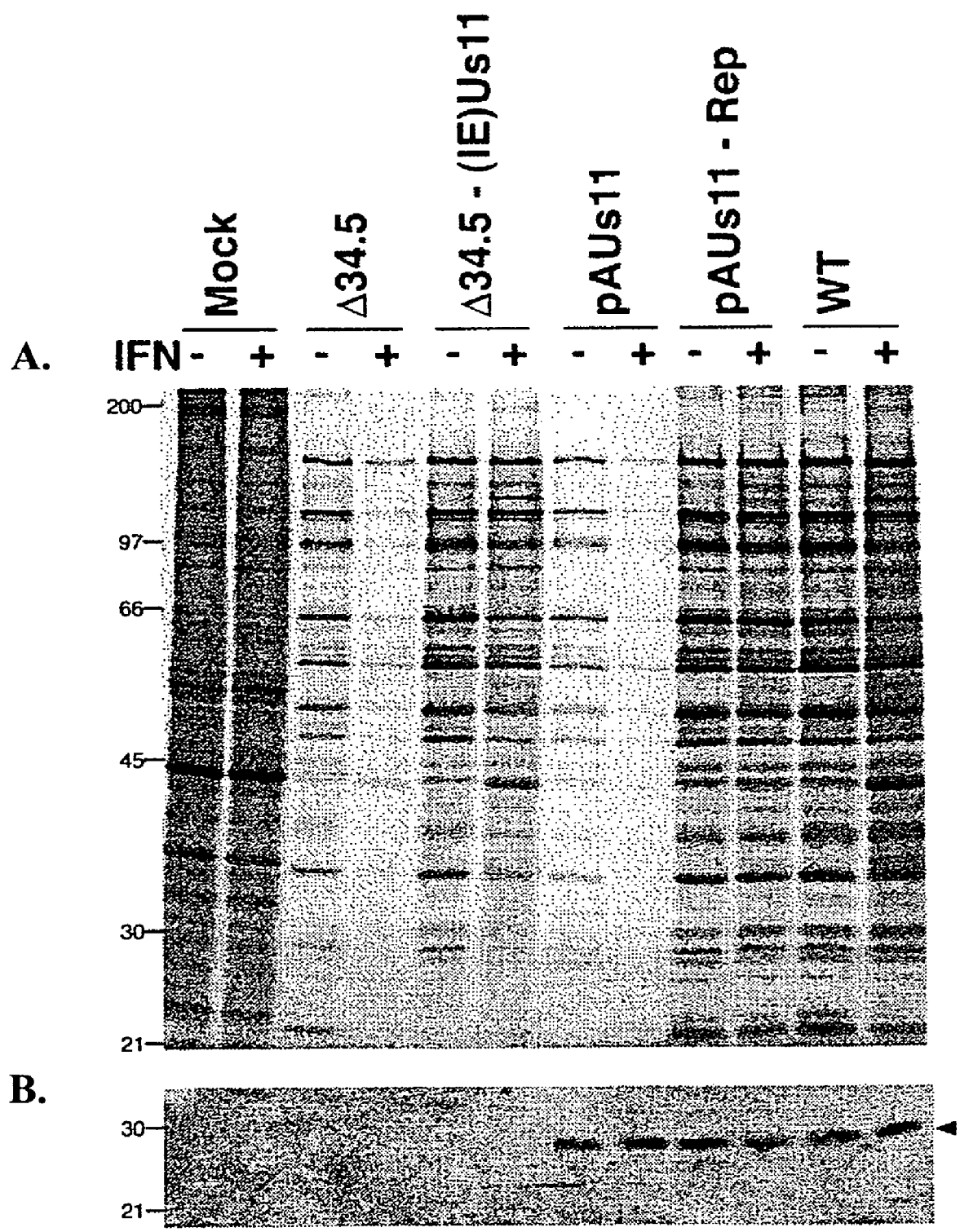
FIGS. 3A-B show the Us11 gene product is required for translation of viral proteins in primary human fibroblasts treated with IFNα. FS4 cells, untreated or treated overnight with human INFα, were mock infected or infected (MOI=5) with either a $\gamma_1 34.5$ deletion mutant (Δ34.5), a Δ34.5 strain that expressed Us11 as an IE protein (Δ34.5-(IE)Us11), a Us11 null mutant (pAUs11), a virus in which the Us11 mutant allele was repaired (pAUs11-Rep), or wild type HSV-1 (WT). At 18 hours post-infection, the cultures were metabolically labeled with $^{35}S$ amino acids for 1 hour. Total protein was isolated and fractionated by SDS-PAGE.

The ability of each mutant virus to sustain late viral protein synthesis following infection of cells in either the presence or absence of IFNα was tested. After primary human foreskin fibroblasts (FS4 cells) were either mock treated or treated with 500 U/ml recombinant human IFNα (Roche Pharmaceuticals, Nutley, N.J.) overnight, they were mock infected or infected (MOI=5) with either wild-type (WT) HSV-1, the γ₁34.5 null mutant Δ34.5, the Δ34.5-(IE)Us11 mutant, the Us11 null mutant, pAUs11, or the pAUs11-Rep mutant virus. Late in the viral life cycle, (18 hrs. post infection) the cultures were metabolically labeled for 1 hour with $^{35}$S amino acids and total protein was subsequently solubilized in SDS-sample buffer (62.5 mM Tris-HCl, pH 6.8, 2% SDS, 10% glycerol, 0.7 M β-mercaptoethanol) prior to fractionation by SDS-PAGE. FIGS. 3A-B establish the role of the Us11 gene in overcoming the innate host defense of IFN. FIG. 3A shows that late viral protein synthesis is resistant to IFNα treatment in cells infected with WT virus, but IFNα sensitive in cells infected with a γ₁34.5 mutant virus and the Us11 null mutant virus. While others have reported that translation in cells infected with a γ₁34.5 mutant is sensitive to IFN (Cerveny et al., "Amino Acid Substitutions In The Effector Domain of The γ₁34.5 Protein of Herpes Simplex Virus 1 Have Differential Effects On Viral Response To Interferon-α," *Virology* 307:290-300 (2003); Cheng et al., "Val$^{193}$ and Phe$^{195}$ of The γ₁34.5 Protein of Herpes Simplex Virus 1 Are Required For Viral Resistance To Interferon α/β," *Virology* 290:115-120 (2001), which are hereby incorporated by reference in their entirety), this is the first time the IFN sensitivity of this mutant has been examined in primary human cells. Further examination of the data immediately revealed that translation ongoing in cells infected with the Us11 null mutant pAUs11 is extremely sensitive to IFNα, while protein synthesis in cells infected with either WT virus, Δ34.5-(IE)Us11, or pAUs11-Rep continues relatively unaffected by the IFN treatment. The observation that translation in cells infected with pAUs11-Rep is resistant to IFNα is particularly important, as it proves that correcting the mutant Us11 allele in the IFN sensitive pAUs11 mutant restores the IFN resistant phenotype, ruling out the possibility that the IFN sensitive phenotype of pAUs11 is due to an adventitious mutation that occurred in the construction of this recombinant.

The apparent resistance of translation rates in cells infected with Δ34.5-(IE)Us11 to IFNα is particularly striking, as this virus contains a complete deletion of both copies of the γ₁34.5 gene, implying that the artificial expression of Us11 as an IE polypeptide can compensate for the loss of the γ₁34.5 protein and maintain viral translation in IFNα-treated cells. Moreover, it supports the observation that translation in cells infected with a Us11 null mutant is hypersensitive to IFN and is consistent with the hypothesis that the dramatic inhibition of translation observed in IFN treated cells infected with a γ₁34.5 mutant is due to the combined loss of both γ₁34.5 and Us11. The important contribution of Us11 is further strengthened by the extreme IFNα sensitivity of translation in cells infected with the pAUs11 mutant, as this virus carries two WT copies of the γ₁34.5 gene and expresses WT levels of the γ₁34.5 protein (Mulvey et al., "Regulation of eIF2α Phosphorylation By Different Functions That Act During Discrete Phases in the HSV-1 Lifecycle," *J Virol* 77:10917-10928 (2003), which is hereby incorporated by reference in its entirety), suggesting that the γ₁34.5 polypeptide on its own is not sufficient to prevent the shutdown of translation in HSV-1 infected primary human cells that have been treated with IFNα.

It was previously established that the premature cessation of translation observed in cells infected with an HSV-1 γ₁34.5 mutant actually results from the absence of the γ₁34.5 gene product and the failure to translate the γ₂ late mRNA which encodes Us11 (Mulvey et al., "Regulation of eIF2α Phosphorylation By Different Functions That Act During Discrete Phases In The HSV-1 Lifecycle," *J Virol* 77:10917-10928 (2003), which is hereby incorporated by reference in its entirety). While viral DNA replication, or a temporally linked event such as the accumulation of late mRNA transcripts, is required for this translational arrest, the reduction of translation rates described here in interferon treated cells infected with a Us11 mutant that produces wild-type levels of the γ₁34.5 protein, may or may not occur with the same kinetics. In particular, overall levels of PKR are greater in interferon treated cells, possibly increasing the responsiveness of this cellular sensor to dsRNA, a molecular indicator of viral infection, and potentially inhibiting translation before the onset of viral DNA replication.

Figure 4:
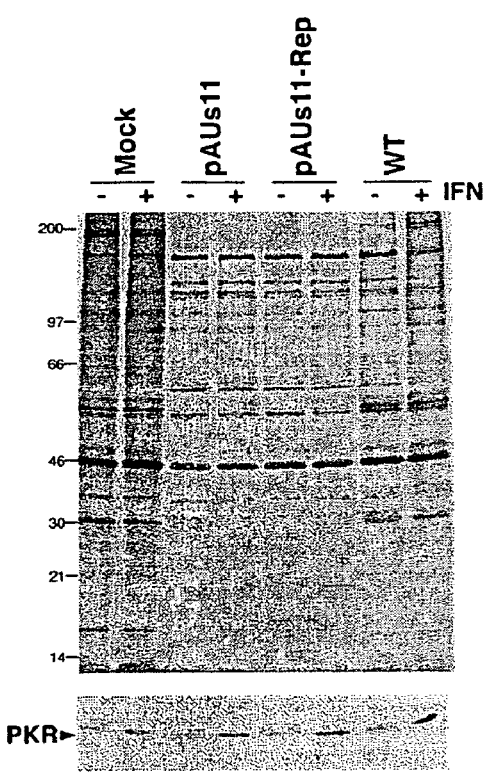
FIGS. 4A-B show the inhibition of translation in IFN treated cells requires entry into the late phase of the viral lifecycle.
Figure 4:
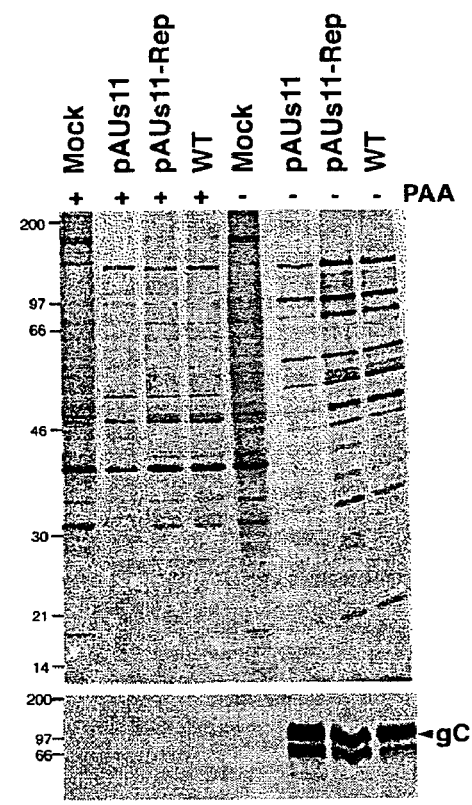

To learn the point in the viral lifecycle at which translation is inhibited in IFN treated cells infected with pAUs11, labeling experiments were performed in cells treated with both IFNα and PAA, an inhibitor of viral DNA synthesis that prevents the lifecycle from advancing into the late phase. The inclusion of IFNα along with PAA in the culture media suppressed the sensitivity of viral translation to IFNα, establishing that the IFN induced translational block observed in cells infected with the pAUs11 mutant virus requires either viral DNA synthesis or a tightly linked event such as the accumulation of true late γ₂ transcripts, as shown in FIG. 4A. As a control to verify that the IFNα treatment was indeed effective in the PAA containing media, the steady state level of PKR was measured, a cellular gene product known to accumulate in response to IFN treatment, by immunoblotting lysates from untreated and interferon treated cells. The increased abundance of PKR in response to IFNα corroborates the effectiveness of this treatment, as shown in FIG. 4A. To confirm that PAA successfully inhibited true-late gene expression, polypeptides synthesized in the presence and absence of PAA were examined. FIG. 4B demonstrates that the pattern of viral proteins synthesized in infected, PAA treated cells differs markedly from those detected in untreated cells; in addition, PAA prevents the reduction in translation rates observed in cells infected with a Us11 mutant virus. Finally, PAA also blocks the accumulation of gC, a known $\gamma_2$, true late polypeptide, as shown in FIG. 4B.

Example 2

Figure 5:
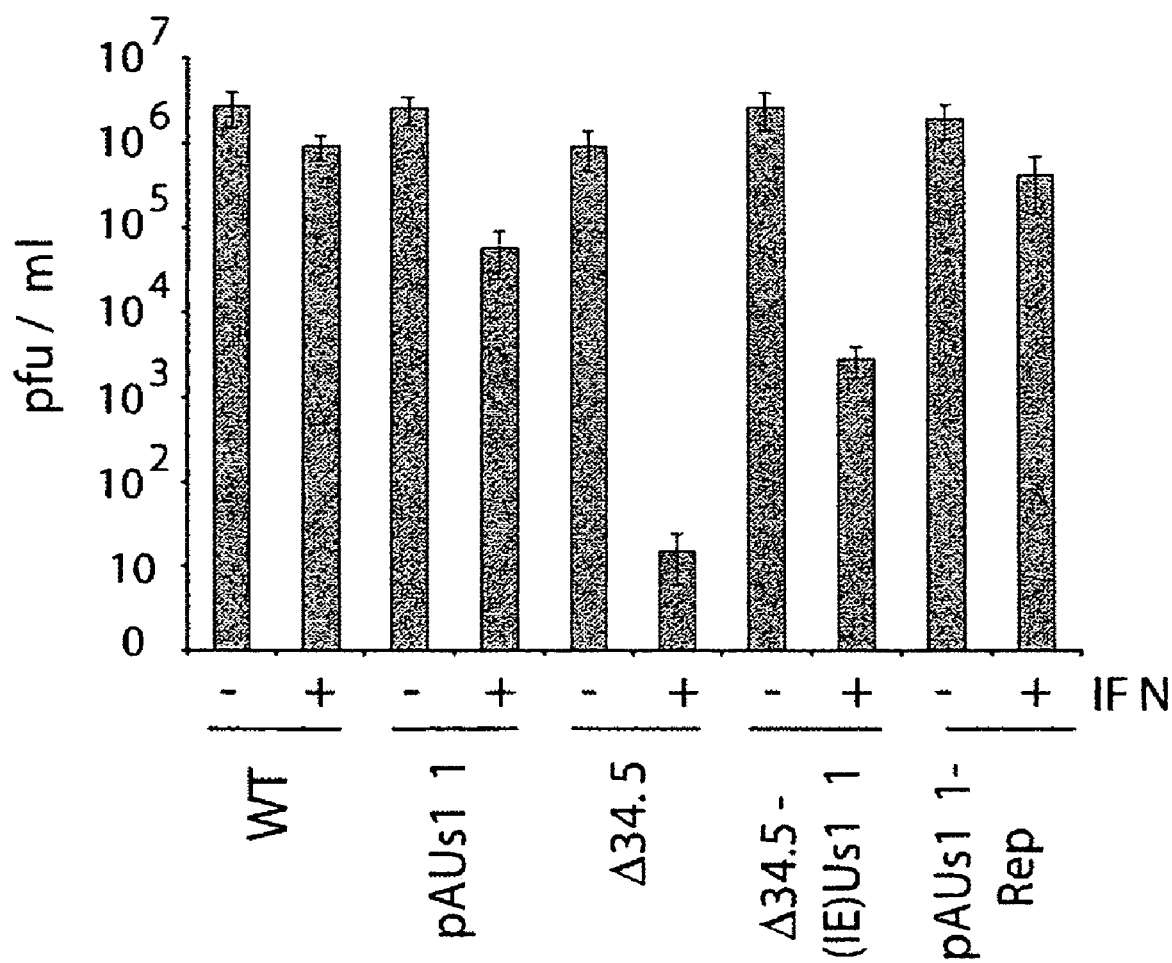
FIG. 5 is a graph showing the replication competence of the indicated viruses (WT vs. modified virus, as described in legend for FIG. 3), in the presence and absence of INFα. FS4 cells, either untreated or treated overnight with 250 U/ml INFα, were infected with the indicated viruses (MOI=$10^{-3}$). After 5 days, cell free lysates were prepared by freeze-thawing the cultures, and the amount of infectious virus produced was quantified by performing a plaque assay in Vero (permissive monkey) cells. The graph indicates that the Us11 gene product is important for wild-type levels of resistance to INFα.

IE Expression of Us11 in Absence of the $\gamma_1 34.5$ Gene Product Supports Viral Replication in IFN α-Treated Cells Prior to evaluating the impact of IFNα treatment on the replication of the mutant viruses in primary FS4 cells, it was observed that commonly used concentrations of IFNα (1000 U/ml) completely inhibited replication of WT HSV-1 in the FS4 cell strain, despite the synthesis of large quantities of viral proteins. Similar findings were reported previously by others working with different strains of fibroblasts and HSV-1. It was noted that treatment with recombinant IFNα or β blocks virus morphogenesis at a late stage and inhibits the release of particles (Chatterjee et al., "Effect of Cloned Human Interferons on Protein Synthesis and Morphogenesis of Herpes Simplex Virus," *J Virol* 56:419-425 (1985), which is hereby incorporated by reference in its entirety). To overcome this obstacle, an IFNα concentration (250 U/ml) was first identified that allowed for the completion of the wild-type HSV-1 lifecycle, with the hope that an IFN sensitive mutant might retain this phenotype under these conditions. After overnight treatment with 250 U/ml IFNα, FS4 cells were infected (MOI=$10^{-3}$) with either WT HSV-1, Δ34.5, Δ34.5 (IE) Us11, pAUs11, or pAUs11-Rep and incubated for 5 days, at which point the cultures were lysed by freeze-thawing and the titer of the virus produced determined in Vero cells. Under these conditions, the genotypically wild-type viruses (WT and pAUs11-Rep) demonstrate between 3-4.7 fold reduction in viral growth following IFNα treatment while, the same treatment results in a 62,000-fold reduction in the growth of the $\gamma_1 34.5$ null mutant Δ34.5, as shown in FIG. 5. It is likely that the magnitude of this difference reflects the failure to translate the true late $\gamma_2$ Us11 mRNA along with the absence of the $\gamma_1 34.5$ gene product in IFNα treated cells infected with the Δ34.5 mutant. Cells infected with the Us11 null mutant pAUs11 exhibited a 44-fold reduction in viral replication following IFNα treatment, establishing that loss of the Us11 gene significantly impairs viral replication in IFNα treated cells. Importantly, pAUs11 still retains the ability to express the $\gamma_1 34.5$ gene product, preventing further reduction in replication under these conditions. In contrast, cultures infected with Δ34.5 IE Us11, a mutant that does not contain a $\gamma_1 34.5$ gene, can only express Us11 as an IE protein to prevent host defenses from inhibiting translation. Here, a 939-fold reduction in replication of Δ34.5-(IE)Us11 was detected in IFNα treated cells. This led to the conclusion that expression of Us11 in the absence of the $\gamma_1 34.5$ gene product supports substantial levels of viral replication in IFNα treated cells, resulting in a 66-fold increase in overall amount of virus produced relative to that for IFNα-treated cells infected with Δ34.5. In addition, the fact that Δ34.5-(IE)Us11 is not as resistant to IFNα as viruses that express the $\gamma_1 34.5$ protein, as shown in FIG. 5, but directs similar rates of translation in primary human cells, as shown in FIGS. 3A-B, and remains neuroattenuated in animal models (Mohr et al., "An HSV-1 γ34.5 Second-Site Suppressor Mutant That Exhibits Enhanced Growth in Cultured Glioblastoma Cells is Severely Attenuated in Animals," *J Virol* 75:5189-5196 (2001), which is hereby incorporated by reference in its entirety) is consistent with the proposal that the $\gamma_1 34.5$ protein performs functions in addition to regulating eIF2α phosphorylation (Brown et al., "ICP34.5 Influences Herpes Simplex Virus Type 1 Maturation and Egress From Infected Cells In Vitro," *J Gen Virol* 75: 3679-3686 (1994), Cheng et al., "Dephosphorylation of eIF2α Mediated By The $\gamma_1 34.5$ Protein of Herpes Simplex Virus Type 1 Is Required For Viral Response To Interferon But Is Not Sufficient For Efficient Viral Replication," *J Virol* 77:10154-10161 (2003), which are hereby incorporated by reference in their entirety).

Taken together, these data suggest that the extreme IFNα-sensitive viral replication observed in primary human fibroblasts infected with Δ34.5 results from the absence of both the viral $\gamma_1 34.5$ and Us11 gene products. By comparing replication of pAUs11, which is a Us11 null mutant with a WT $\gamma_1 34.5$ gene, with Δ34.5-(IE)Us11, which is a $\gamma_1 34.5$ null mutant that expresses Us11 as an IE gene, it is shown that both of these gene products contribute significantly to the ability of HSV-1 to replicate in IFNα-treated cells and that both are required for WT levels of replication in IFN-treated primary human cells. This is the first demonstration that the Us11 gene product contributes to HSV-1 replication in IFN-treated cells, raising the possibility that it might also perform a similar role in viral pathogenesis.

Example 3

Evaluation of Anti-Tumor Activity of Us11-IE Mutant

Figure 6:
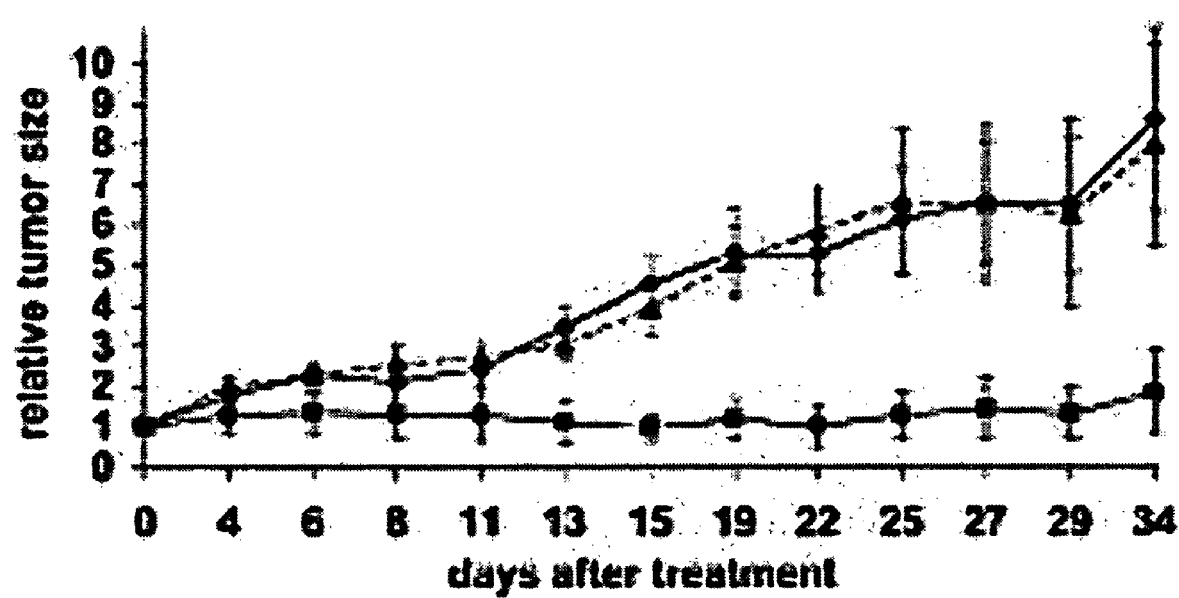
FIG. 6 is a graph evaluating the anti-tumor potential of a replication-competent HSV-1 modified virus engineered for IE expression of Us11. Balb/c/nu mice (n=5 for each treatment group) harboring established, s.c. PC3 tumors measuring≈50 mm$^3$ received a single injection containing 2×10$^6$ pfu of either the γ34.5 deletion mutant Δ34.5 (▲, broken line), the suppressor Δ34.5-(IE)Us11 mutant, (■), or a virus-free lysate prepared from mock-infected cells (♦). Tumors were measured every 2 days for 34 days and the average normalized values reflecting relative tumor size each day were plotted. The initial tumor volume immediately before treatment was normalized to a relative size of 1.0. Error bars reflect the SEM.

To evaluate the ability of the early expressing Us11 mutant to reduce the growth of tumors in vivo, s.c. xenografts of human PC3 prostate carcinoma cells were established in immunocompromised (nude) mice (Taneja et al., "Enhanced Antitumor Efficacy of a Herpes Simplex Virus Mutant Isolated by Genetic Selection in Cancer Cells," *Proc Natl Acad Sci USA* 98:8804-8808 (2001), which is hereby incorporated by reference in its entirety). Once the implanted tumors reached ≈50 mm$^3$ in volume, they were challenged by a single injection ($2 \times 10^6$ pfu) of either the Δ34.5 virus, the Δ34.5-(IE)Us11 suppressor mutant, or a virus-free lysate prepared from mock infected cells. FIG. 6 shows that Δ34.5 was not effective in reducing the growth of the xenograft (P>0.5 for Δ34.5 vs. mock at $2 \times 10^6$ pfu). The Δ34.5-(IE)Us11 suppressor mutant however, was significantly more effective in inhibiting the growth of PC3 xenografts at this dose than was the Δ34.5 mutant (P<0.05 for Δ34.5-(IE)Us11 vs. Δ34.5).

Example 4

Preparation of Δ34.5::f1Δ27P-Us11 HSV-1 Mutant

Figure 7A:
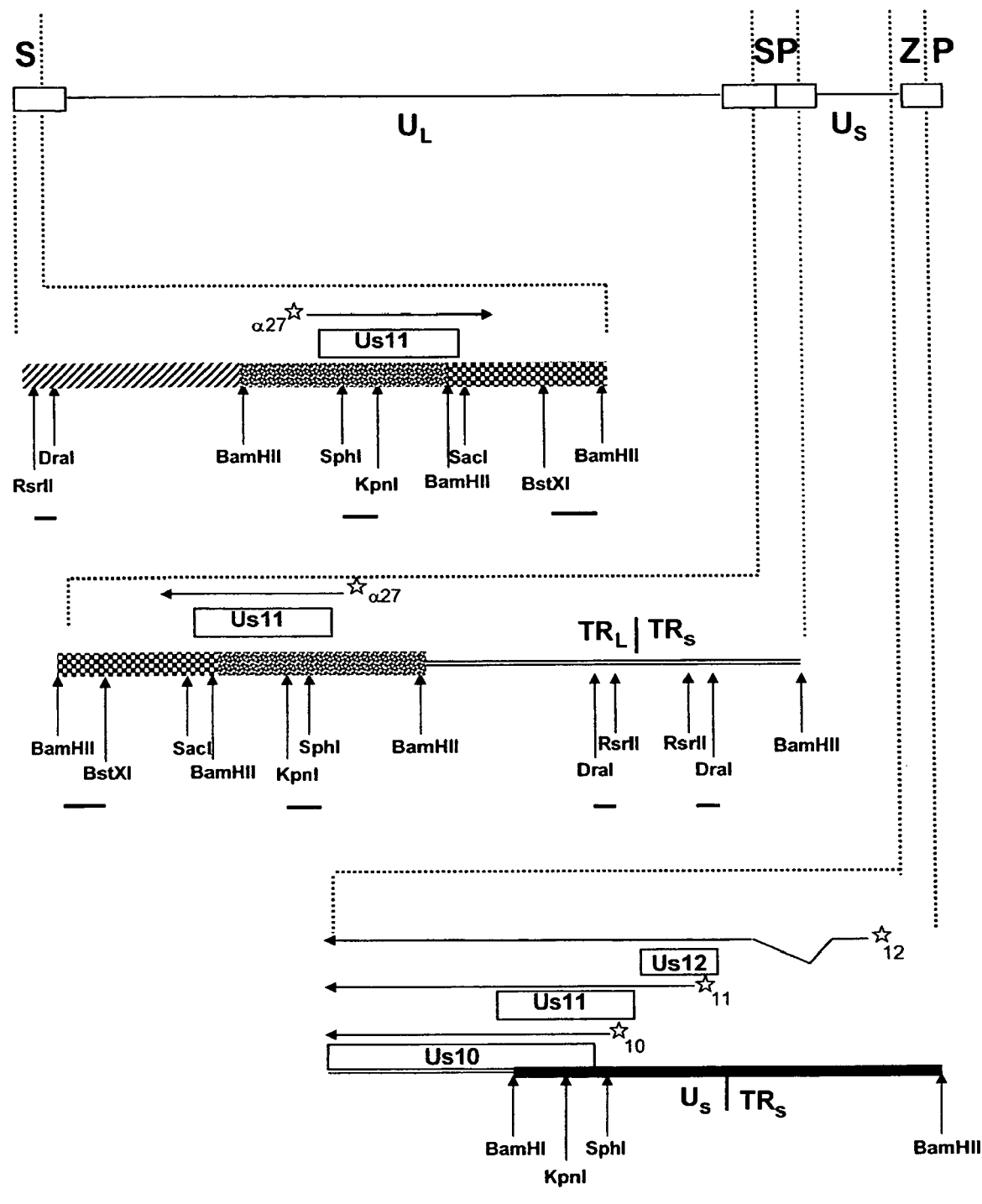
FIGS. 7A-B are maps of the genome of the Δ34.5::f1α27P-Us11 modified virus of the present invention.
Figure 7B:
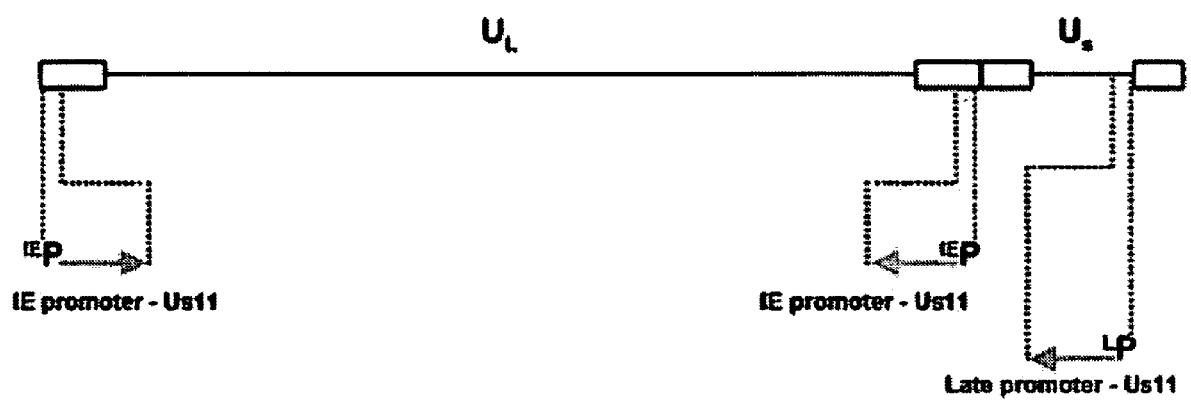

Based on the studies described above, a new, modified HSV-1 vector was designed that improved upon the previously made oncolytic mutants. To generate an avirulent Δ34.5 virus that expresses Us11 at immediate early (IE) times and preserves the immunomodulatory Us12 gene, both the $\gamma_1 34.5$ promoter and ORF of the HSV-1 genome were replaced by cloning the Us11 gene, under transcriptional control of the α27 IE promoter, between the DraI and SacI sites of Bam SP, as shown in FIG. 7A. This fragment was cotransfected into Vero cells with purified Δ34.5 virus DNA and recombinants were selected on U373 glioblastoma cells, which are non-permissive for the growth of Δ34.5 viruses that do not express Us11 at IE times. This modified virus was named: Δ34.5:: f1α27P-Us11. FIG. 7A is a detailed map of the genome of the Δ34.5::f1Δ27P-Us11 modified virus of the present invention, including restriction sites, and shows the location of the Us11 genes that have replaced the two WT $\gamma_1 34.5$ genes, while leaving intact the Us10, Us11 and Us12 loci. Thus, the modified $\Delta 34.5$::f1$\alpha$27P-Us11 of the present invention has three functional Us11 genes, as shown in the simplified line diagram of $\Delta 34.5$::f1$\alpha$27P-Us11 provided in FIG. 7B.

Figure 8:
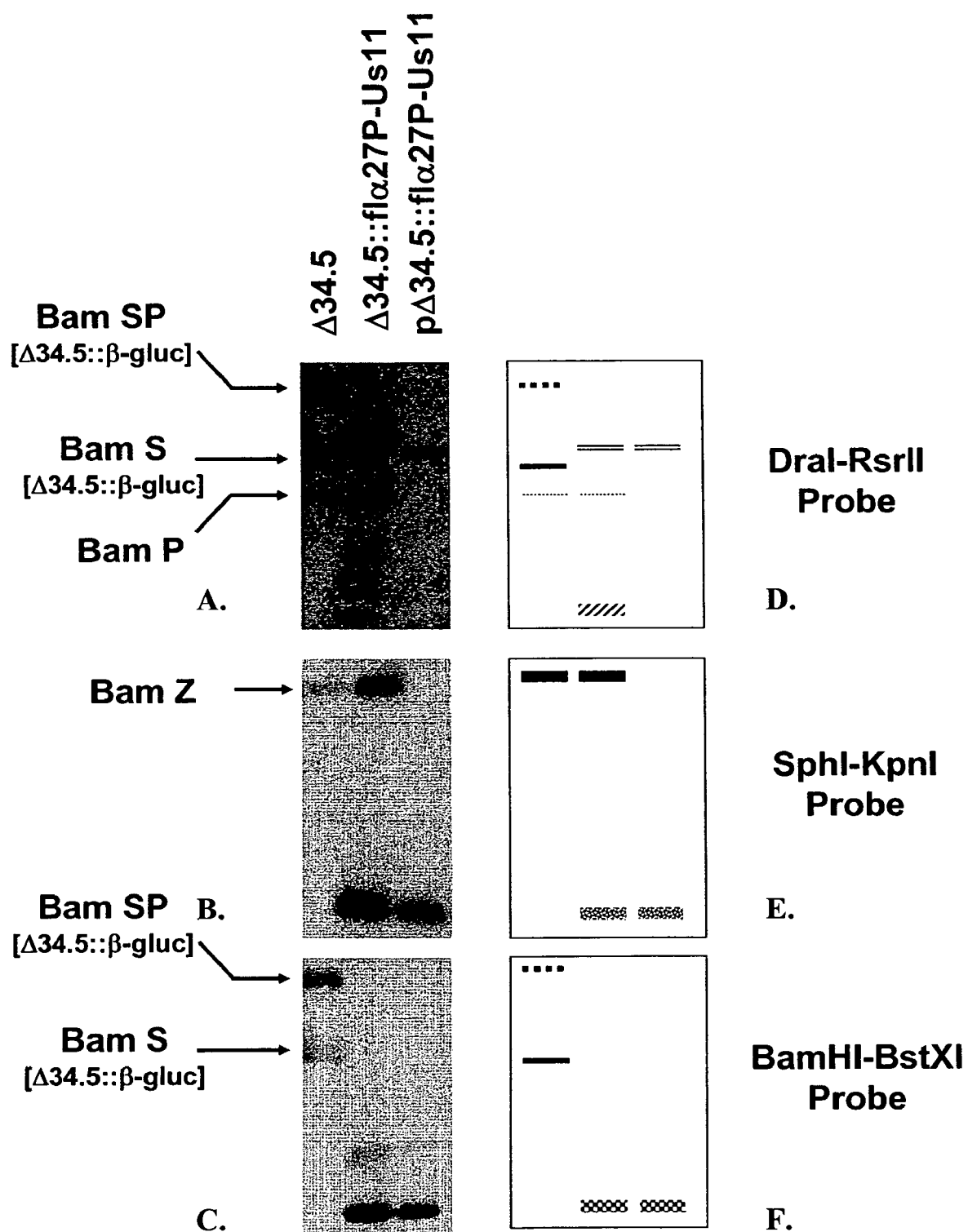
FIGS. 8A-F are immunoblots of the restriction digest experiments, shown in FIGS. 8A-C, and corresponding cartoons, FIG. 8D-F, interpreting the digestion study following the making of the US11 gene in the modified virus. The line marking of FIGS. 8D, 8E, and 8F refer back to the markings of the genome diagram in FIG. 7A.

To verify the genetic structure of $\Delta 34.5$::f1$\alpha$27P-Us11, a BamHI restriction enzyme digestion was performed on isolated $\Delta 34.5$, and $\Delta 34.5$::f1$\alpha$27P-Us11 viral DNA (vDNA) as well as the targeting plasmid, p$\Delta 34.5$::f1$\alpha$27P-Us11, as shown in FIGS. 8A-F. The BamHI restriction pattern of $\Delta 34.5$::f1$\alpha$27P-Us11 vDNA is complicated. Therefore, the various restriction fragments are coded in the exploded views (designated by dotted lines) of FIGS. 2B and 7A to facilitate interpretation of the southern blots shown in FIGS. 8D, 8E, and 8F. The digested plasmid DNA was separated on a 1% Agarose/TAE gel and blotted onto a nytran-N nylon membrane. BamHI digestion of $\Delta 34.5$ vDNA yields two easily separable fragments that wholly contain the $\Delta 34.5$::$\beta$-gluc loci. However, the corresponding BamHI fragments in $\Delta 34.5$::f1$\alpha$27P-Us11 have internal BamHI sites which cut the $\Delta 34.5$::f1$\alpha$27P-Us11 loci into three fragments. Two of these fragments are constant in size irrespective of the $\gamma 34.5$ locus in which they reside. The third fragment, which differs in size depending on the $\gamma 34.5$ locus in which it resides, can be detected using the DraI-RsrII probe, as shown in FIGS. 8A and 8D. This probe detects the Bam S, P, and SP fragments as is observed in the $\Delta 34.5$ lane. In the $\Delta 34.5$::f1$\alpha$27P-Us11 lane, the $\Delta 34.5$::$\beta$-gluc loci in Bam S and SP are not observed. Instead, two new fragments are present. The slowest migrating fragment corresponds to the $\Delta 34.5$::f1$\alpha$27P-Us11 Bam SP terminus and comigrates with p$\Delta 34.5$::f1$\alpha$27P-Us11 control. The fastest migrating band corresponds to the $\Delta 34.5$::f1$\alpha$27P-Us11 Bam S terminus, shown as a solid black line, medium thickness in FIG. 8D. The second slowest migrating fragment in the $\Delta 34.5$::f1$\Delta$27P-Us11 lane comigrates with a band in the $\Delta 34.5$ lane, for that band is the Bam P fragment which is not rearranged in $\Delta 34.5$::f1$\alpha$27P-Us11. Bam P is shown as a thin dotted line in FIG. 8D. The bands in the $\Delta 34.5$ and $\Delta 34.5$::f1$\Delta$27P-Us11 lanes are heterogeneous due to varying iterations of a repetitive sequence located at the termini of the inverted repeats in DNA isolated from virally infected cells. This heterogeneity is not observed in the p$\Delta 34.5$::f1$\alpha$27P-Us11 control because this is a cloned plasmid, not vDNA. The $\Delta 34.5$::f1$\Delta$27P-Us11 virus is triploid for the Us11 ORF, as verified by probing the southern blot with the Us11-specific SphI-KpnI probe, as shown in FIGS. 8B and 8E. The slowest migrating band in the $\Delta 34.5$::f1$\alpha$27P-Us11 lane corresponds to the Bam Z, shown as a thick black line in FIG. 8E, of the fragment which contains the bonafide Us11 locus. The fastest migrating band in the $\Delta 34.5$::f1$\Delta$27P-Us11 lane comigrates with the p$\Delta 34.5$::f1$\alpha$27P-Us11 control and corresponds to the Us11 ORF located at both $\gamma 34.5$ loci. The diploid nature of this fragment is verified by the observation that the fastest migrating band in the $\Delta 34.5$::f1$\Delta$27P-Us11 lane is present at approximately twice the concentration of the haploid Bam Z fragment in the same lane. The Bam S and SP specific BamHI-BstXI probe detects the third internal fragment of the $\Delta 34.5$::f1$\alpha$27P-Us11 loci. This fragment is constant in size irrespective of the $\gamma 34.5$ loci in which it resides. Therefore, in the southern blot incubated with the BamHI-BstXI probe, there is only one fragment in the $\Delta 34.5$:: f1$\Delta$27P-Us11 lane and it comigrates with the p$\Delta 34.5$:: f1$\Delta$27P-Us11 control but not with the Bam S and SP fragments in the $\Delta 34.5$ lane, as shown in FIGS. 8C and 8F.

Example 5

$\Delta 34.5$::f1$\Delta$27P-Us11 Virus Produces the Us11 Protein as IE Protein

Figure 9:
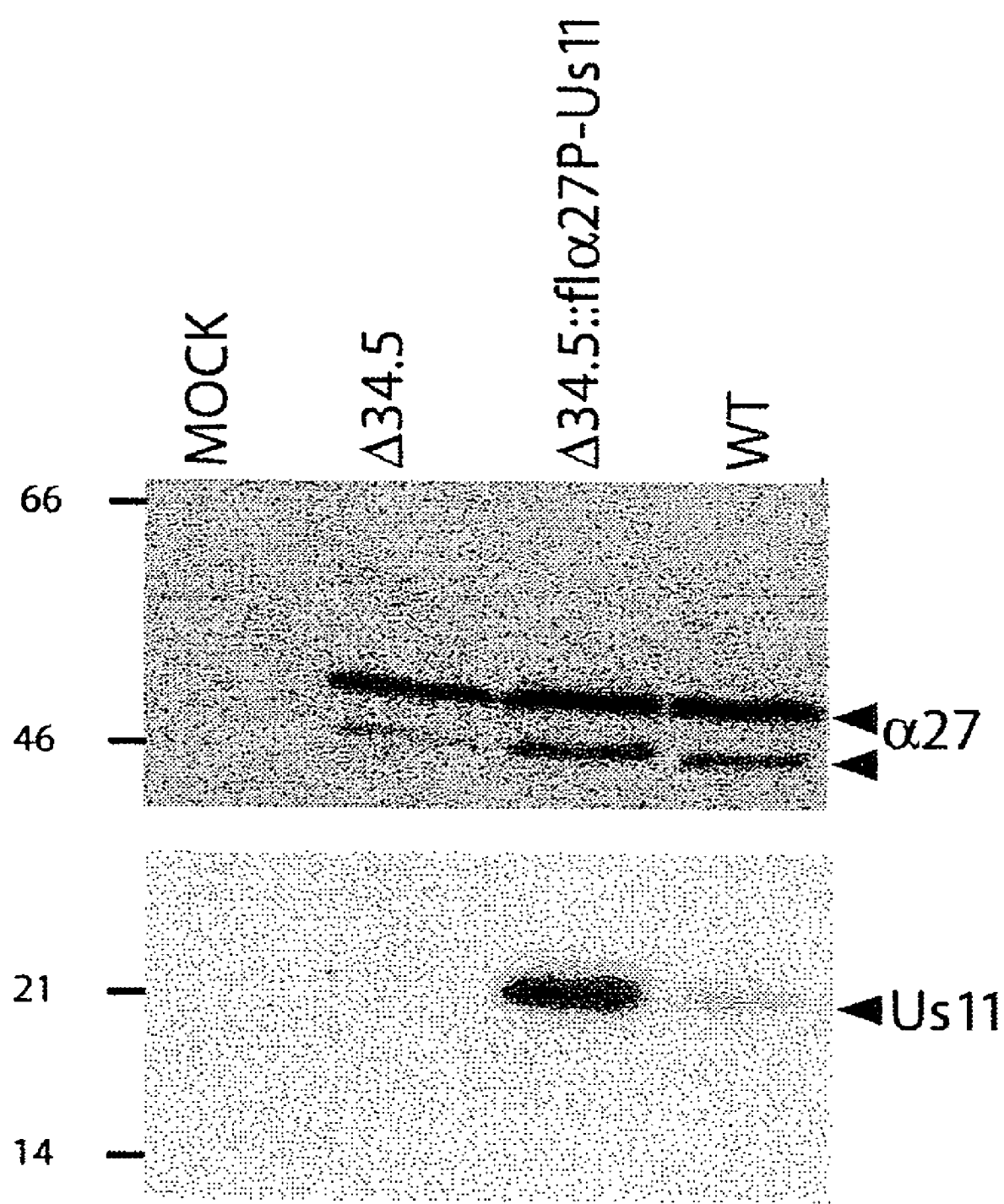
FIG. 9 is an immunoblot demonstrating that the Δ34.5::f1α27P-Us11 virus of the present invention produces the Us11 protein as an immediate-early protein. U373 human glioblastoma cells were mock infected (MOCK) or infected (MOI=5) with either a $\gamma_1$34.5 deletion mutant (Δ34.5), Δ34.5::f1α27P-Us11 or wild-type HSV-1 (WT). Molecular weight standards (in kDa) are indicated to the left of the panel.

U373 human glioblastoma cells were mock infected (MOCK) or infected (MOI=5) with either a $\gamma_1 34.5$ deletion mutant ($\Delta 34.5$), the $\Delta 34.5$::f1$\Delta$27P-Us11 mutant or wild-type HSV-1 (WT). At 6 hours post-infection, total protein was isolated and fractionated by SDS-PAGE. After transfer of the proteins to a membrane support, the filter was cut into two pieces, probed with antisera against the HSV-1 $\Delta 27$ immediate early protein or the Us11 "true-late" or $\gamma_2$ polypeptide, and the proteins were visualized following incubation with a horse radish peroxidase conjugated secondary antibody. FIG. 9 shows the immunoblot demonstrating the $\Delta 34.5$::f1$\alpha$27P-Us11 virus produces the Us11 protein as an immediate-early protein. Molecular weight standards (in kDa) are indicated to the left of the panel. While similar amounts of the $\alpha 27$ gene product are visible in all of the infected samples, Us11 is most abundant in cells infected with $\Delta 34.5$::f1$\Delta$27P-Us11. The small quantity of Us11 protein visible in cells infected with WT virus reflects the advance of a small subpopulation of infected cells into the late phase of the viral lifecycle.

Example 6

Figure 10:
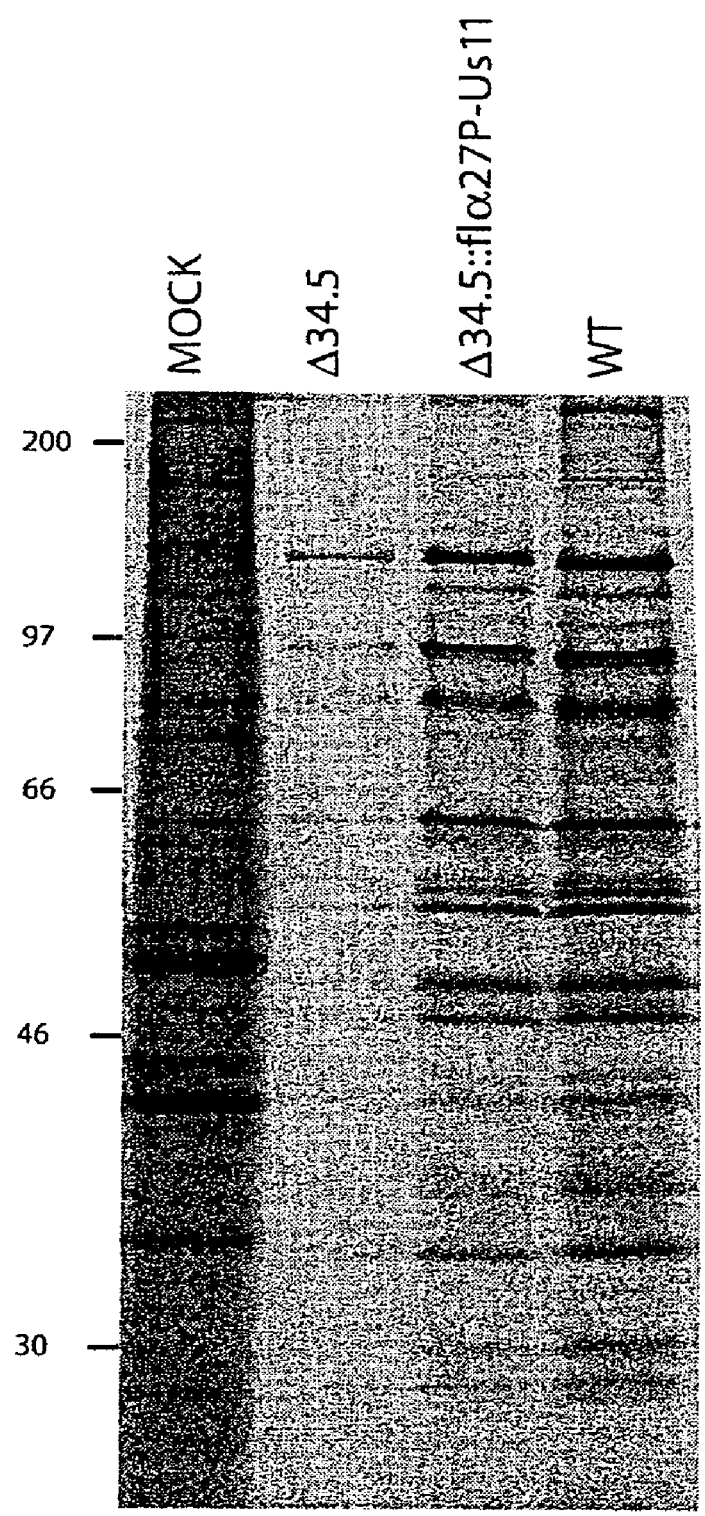
FIG. 10 is an autoradiogram of an SDS-polyacrylamide gel showing that translation rates in cells infected with Δ34.5::f1α27P-Us11 are nearly restored to levels seen in cells infected with WT virus. U373 human glioblastoma were mock infected (MOCK), or infected (MOI=5) with either a $\gamma_1$34.5 deletion mutant (Δ34.5), Δ34.5::f1α27P-Us11 or wild-type HSV-1 (WT). Molecular weight standards (in kDa) are indicated to the left of the panel.

$\Delta 34.5$::f1$\Delta$27P-Us11 Restores Ability to Translate Viral Proteins to $\Delta 34.5$ Mutant FIG. 10 displays an autoradiogram of an SDS-polyacrylamide gel demonstrating that translation rates in cells infected with $\Delta 34.5$::f1$\Delta$27P-Us11 are nearly restored to levels seen in cells infected with WT virus. U373 human glioblastoma were mock infected (MOCK), or infected (MOI=5) with either a $\gamma_1 34.5$ deletion mutant ($\Delta 34.5$), $\Delta 34.5$::f1$\Delta$27P-Us11 or wild-type HSV-1 (WT). At 13 hours post-infection, the cells were radiolabeled for 1 hour with $^{35}$S cysteine and methionine. After whole cell extracts were prepared in SDS sample buffer, proteins were fractionated by SDS-PAGE and the fixed, dried gel was exposed to Kodak XAR film. The $\Delta 34.5$ mutant is unable to counter host defenses, and translation of viral proteins is inhibited prior to the completion of the viral lifecycle. In contrast, $\Delta 34.5$::f1$\Delta$27P-Us11 produces the Us11 protein during the immediate-early phase of the viral lifecycle. Thus, the Us11 gene product effectively counters host defenses and enables the sustained translation of viral mRNAs.

Example 7

Figure 11:
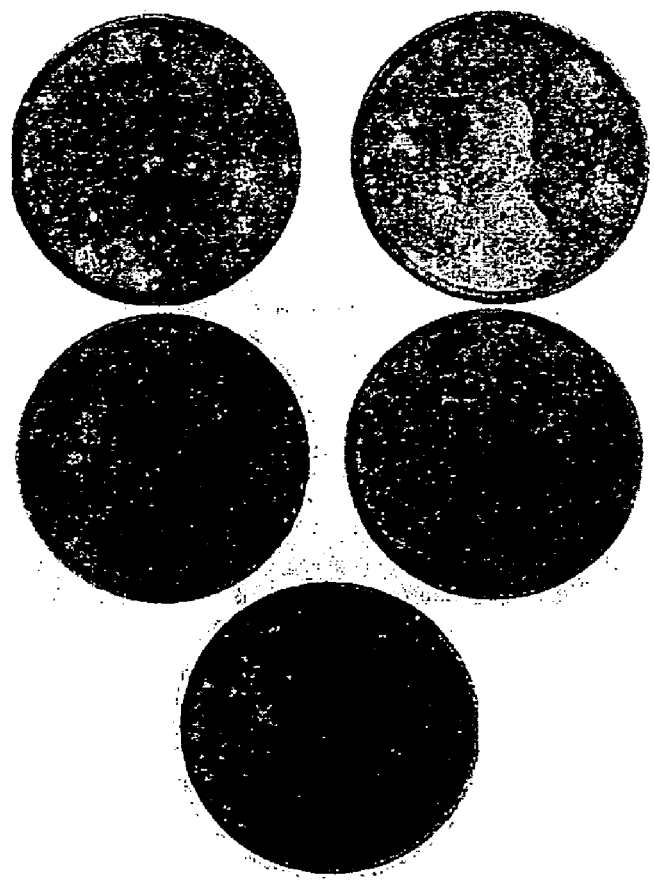
FIG. 11 are photographs of a plaque assay comparing the replicative competence of the Δ34.5::f1Δ27P-Us11 virus versus the simple $\gamma_1$34.5 deletion mutant in human cancer cells.

$\Delta 34.5$::f1$\Delta$27P-Us11 Replication in Human Cancer Cells is Superior to Simple $\gamma_1 34.5$ Deletion Mutant Viral DNA from a $\Delta 34.5$ mutant was transfected alone or cotransfected with one of two plasmids containing a modified HSV-1 BamHI SP fragment into permissive Vero cells using the calcium phosphate technique. Both plasmids contain an expression cassette inserted in place of sequences between the DraI (nucleotide #'s 125990) and SacI (nucleotide #'s 125068) (nucleotide numbers refer to GenBank Accession No. X14112, HSV-1 sequenced strain 17 in particular) sites in the BamHI SP fragment. In one plasmid, p$\Delta 34.5$::f1$\alpha$27P-Us11, the expression cassette is composed of the Us11 ORF fused to the HSV-1 Δ27 promoter. The other plasmid, pΔ34.5, is isogenic to pΔ34.5::f1α27Pfs-Us11 except for a single nucleotide insertion at codon 3 of the Us11 ORF. Once plaques appeared, a cell-free lysate was prepared by freeze-thawing, and dilutions were used to infect non-permissive U373 cells. After a single pass of the transfection lysate on U373 cells, the viral stock was diluted and used to infect duplicate 60-mm-diameter dishes of freshly confluent U373 cells. Only one 60 mm dish was used for the Δ34.5 control sample. After 3 days, these dishes were fixed and stained with crystal violet. Plaques, representing areas of viral replication, were only seen in cultures transfected with the pΔ34.5::f1α27P-Us11 plasmid. Significantly, a frame-shift mutation which prevents the synthesis of the Us11 polypeptide abrogates plaque formation, demonstrating that a functional Us11 protein is required to counteract host defenses and enable efficient viral replication. As shown in FIG. 11, a virus engineered such that i) both $\gamma_1 34.5$ genes are each replaced by an expression cassette directing the production of the Us11 gene product during the immediate-early phase of the viral life-cycle; ii) it contains a third copy of the Us11 gene expressed from a late promoter; and iii) retains an intact Us12 gene that expresses the IPC47 immunomodulatory protein, replicates more effectively in human cancer cells than a virus containing a simple deletion of both $\gamma_1 34.5$ genes.

The $\gamma_1 34.5$ gene product is important for the resistance of HSV-1 to interferon. However, since the inhibition of protein synthesis observed in cells infected with a $\gamma_1 34.5$ mutant virus results from the combined loss of the $\gamma_1 34.5$ gene product and the failure to translate the late Us11 mRNA, relative interferon sensitivity of mutants unable to produce either the Us11 or the $\gamma_1 34.5$ polypeptides were characterized. It is demonstrated herein, above, that primary human cells infected with a Us11 mutant herpes simplex virus are hypersensitive to interferon $\alpha/\beta$, arresting translation upon entry into the late phase of the viral life cycle. Furthermore, immediate-early expression of Us11 by a $\gamma_1 34.5$ deletion mutant is sufficient to render translation resistant to $\alpha/\beta$. Finally, it is established for the first time herein that the Us11 gene product is required for wild-type levels of replication in $\alpha/\beta$ treated cells and along with the $\gamma_1 34.5$ gene, is an HSV-1 encoded interferon resistance determinant.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An avirulent, oncolytic herpes simplex virus having an intact $U_s 12$ gene and an endogenous $U_s 11$ gene expressed as a late gene, wherein said virus is modified from the wild-type herpes simplex virus with both $\gamma_1 34.5$ genes of the virus being deleted and $U_s 11$ genes that are expressed as immediate-early (IE) genes being inserted into the $\gamma_1 34.5$ gene locus in place of both $\gamma_1 34.5$ genes.

2. The oncolytic modified virus according to claim 1, wherein the interferon-resistance gene is under the control of a herpes simplex virus (IE) promoter.

3. The oncolytic modified virus according to claim 2, wherein the promoter is an α27 IE promoter.

4. The oncolytic modified herpes simplex virus according to claim 1 further comprising an ICP 6-inactivating mutation.

5. The oncolytic modified virus according to claim 1, wherein the wild-type herpes simplex virus is herpes simplex virus type 1 (HSV-1).

6. The oncolytic modified virus according to claim 5, wherein the HSV-1 is a strain selected from the group consisting of HSV-1 strain 17, strain KOS, strain F, strain Patton, and any clinical isolate.

7. A pharmaceutical composition comprising:
the avirulent, oncolytic modified herpes simplex virus according to claim 1, and a pharmaceutically acceptable vehicle for in situ administration to tumor cells.

8. The pharmaceutical composition according to claim 7, wherein the wild-type herpes simplex virus is herpes simplex virus type 1.

9. A method for killing tumor cells in a subject comprising:
administering to a subject the avirulent, oncolytic modified herpes simplex virus according to claim 1 under conditions effective to kill tumor cells in the subject.

10. The method according to claim 9, wherein the tumor cells are selected from the group consisting of astrocytoma, oligodendroglioma, meningioma, neurofibroma, glioblastoma, ependymoma, Schwannoma, neurofibrosarcoma, medulloblastoma, melanoma cells, pancreatic cancer cells, prostate carcinoma cells, breast cancer cells, lung cancer cells, colon cancer cells, lymphoma cells, hepatoma cells, mesothelioma and epidermoid carcinoma cells.

11. The method according to claim 9, wherein the administering is carried out by injection, infusion, instillation or inhalation.

12. The method according to claim 9, wherein the subject is a mammal.

13. The method according to claim 12, wherein the mammal is a human.

* * * * *